(12) United States Patent
Wainwright et al.

(10) Patent No.: US 9,750,623 B2
(45) Date of Patent: *Sep. 5, 2017

(54) VASCULAR STENT WITH IMPROVED VESSEL WALL APPOSITION

(71) Applicant: COVIDIEN LP, Mansfield, MA (US)

(72) Inventors: John Wainwright, Rancho Santa Margarita, CA (US); Jianlu Ma, Irvine, CA (US); Michael Losordo, San Juan Capistrano, CA (US)

(73) Assignee: Covidien LP, Manfield, MA (US)

( * ) Notice: Subject to any disclaimer, the term of this patent is extended or adjusted under 35 U.S.C. 154(b) by 107 days.

This patent is subject to a terminal disclaimer.

(21) Appl. No.: 14/693,921

(22) Filed: Apr. 23, 2015

(65) Prior Publication Data
US 2015/0290005 A1    Oct. 15, 2015

Related U.S. Application Data

(63) Continuation of application No. 13/428,822, filed on Mar. 23, 2012, now Pat. No. 9,028,540.
(Continued)

(51) Int. Cl.
*A61F 2/82*    (2013.01)
*A61F 2/95*    (2013.01)
(Continued)

(52) U.S. Cl.
CPC .......... *A61F 2/915* (2013.01); *A61B 17/1214* (2013.01); *A61B 17/12031* (2013.01);
(Continued)

(58) Field of Classification Search
CPC ...... A61F 2/82; A61F 2/86; A61F 2/90; A61F 2/91; A61F 2/915; A61F 2/95;
(Continued)

(56) References Cited

U.S. PATENT DOCUMENTS 5,800,520 A    9/1998 Fogarty et al.
6,129,755 A    10/2000 Mathis et al.
(Continued)

FOREIGN PATENT DOCUMENTS

EP    887051 A1    12/1998
EP    928606 A1    7/1999
(Continued)

*Primary Examiner* — Ryan J Severson
(74) *Attorney, Agent, or Firm* — Mark Kertz

(57) ABSTRACT

A medical device is provided. The medical device includes a vessel-engaging member attached to a distal end of a delivery wire via a connection mechanism. The vessel-engaging member includes a plurality of rows and a plurality of bridges positioned between each adjacent row, each of the bridges connecting a vertex of a first row with a corresponding vertex of a second row. The vessel-engaging member further includes first and second tapered sections coupled to the connection mechanism, each of the tapered sections projecting from a proximal row and tapering in a direction from the proximal row toward the connection mechanism, each of the tapered sections having a length measured along a longitudinal axis, wherein the length of the first tapered section is less than the length of the second tapered section.

19 Claims, 12 Drawing Sheets

Related U.S. Application Data

(60) Provisional application No. 61/467,916, filed on Mar. 25, 2011.

(51) Int. Cl.
  *A61F 2/915* (2013.01)
  *A61F 2/92* (2013.01)
  *A61B 17/12* (2006.01)
  *A61F 2/848* (2013.01)

(52) U.S. Cl.
  CPC ........ *A61B 17/12118* (2013.01); *A61F 2/848* (2013.01); *A61F 2/92* (2013.01); *A61F 2/95* (2013.01); *A61F 2002/823* (2013.01); *A61F 2002/9155* (2013.01); *A61F 2002/91575* (2013.01); *A61F 2002/9505* (2013.01); *A61F 2002/9511* (2013.01); *A61F 2002/9528* (2013.01); *A61F 2002/9534* (2013.01); *A61F 2230/0054* (2013.01); *A61F 2250/0036* (2013.01)

(58) Field of Classification Search
  CPC .......... A61F 2002/823; A61F 2002/825; A61F 2002/91508; A61F 2002/91516; A61F 2002/91525; A61F 2002/91533; A61F 2002/91541; A61F 2002/9155; A61F 2002/91558; A61F 2002/91566; A61F 2002/91575; A61F 2002/91583; A61F 2002/9505; A61F 2002/9522; A61F 2002/9528; A61F 2002/9534
  See application file for complete search history.

(56) References Cited

U.S. PATENT DOCUMENTS

| | | | |
|---|---|---|---|
| 6,132,461 A | 10/2000 | Thompson | |
| 6,190,406 B1 | 2/2001 | Duerig et al. | |
| 6,235,053 B1 | 5/2001 | Jang | |
| 6,241,738 B1 | 6/2001 | Dereume | |
| 6,342,067 B1 | 1/2002 | Mathis et al. | |
| 6,524,337 B1 | 2/2003 | Bergeron | |
| 6,533,808 B1 | 3/2003 | Thompson | |
| 6,558,415 B2 | 5/2003 | Thompson | |
| 6,673,106 B2 | 1/2004 | Mitelberg et al. | |
| 6,764,507 B2 | 7/2004 | Shanley et al. | |
| 6,818,013 B2 | 11/2004 | Mitelberg et al. | |
| 6,884,260 B2 | 4/2005 | Kugler et al. | |
| 6,939,371 B2 | 9/2005 | Kugler et al. | |
| 7,300,458 B2 | 11/2007 | Henkes et al. | |
| 7,309,351 B2 | 12/2007 | Escamilla et al. | |
| 7,335,224 B2 | 2/2008 | Ohlenschlaeger | |
| 7,442,203 B2 | 10/2008 | Ehr et al. | |
| 7,556,644 B2 | 7/2009 | Burpee et al. | |
| 7,618,445 B2 | 11/2009 | Moriuchi et al. | |
| 7,632,300 B2 | 12/2009 | Thompson | |
| 7,763,064 B2 | 7/2010 | Pinchasik | |
| 7,803,180 B2 | 9/2010 | Burpee et al. | |
| 7,896,912 B2 | 3/2011 | Shanley | |
| 7,988,723 B2 | 8/2011 | Beach et al. | |
| 7,993,383 B2 | 8/2011 | Hartley et al. | |
| 8,007,528 B2 | 8/2011 | Yadin et al. | |
| 8,048,146 B2 | 11/2011 | Young et al. | |
| 8,066,757 B2 | 11/2011 | Ferrera et al. | |
| 8,465,436 B2 | 6/2013 | Griswold | |
| 8,500,794 B2 | 8/2013 | Beach et al. | |
| 8,540,761 B2 | 9/2013 | Rabkin et al. | |
| 8,540,763 B2 | 9/2013 | Jones et al. | |
| 8,663,309 B2 | 3/2014 | Chobotov | |
| 9,028,540 B2 | 5/2015 | Wainwright et al. | |
| 9,254,205 B2 * | 2/2016 | Wainwright ..... | A61B 17/12118 |
| 2002/0042647 A1 | 4/2002 | Jang | |
| 2002/0128707 A1 | 9/2002 | Kavteladze et al. | |
| 2002/0188341 A1 | 12/2002 | Elliott | |
| 2002/0193862 A1 | 12/2002 | Mitelberg et al. | |
| 2002/0198587 A1 | 12/2002 | Greenberg et al. | |
| 2003/0176914 A1 | 9/2003 | Rabkin et al. | |
| 2003/0187497 A1 | 10/2003 | Boylan et al. | |
| 2003/0196717 A1 | 10/2003 | Nunez et al. | |
| 2004/0015226 A1 | 1/2004 | Pelton | |
| 2004/0015228 A1 | 1/2004 | Lombardi et al. | |
| 2004/0034402 A1 | 2/2004 | Bales et al. | |
| 2004/0039435 A1 | 2/2004 | Hancock et al. | |
| 2004/0111147 A1 | 6/2004 | Rabkin et al. | |
| 2004/0230291 A1 | 11/2004 | Richter | |
| 2005/0080479 A1 | 4/2005 | Feng et al. | |
| 2005/0125051 A1 | 6/2005 | Eidenschink et al. | |
| 2005/0172471 A1 | 8/2005 | Vietmeier | |
| 2005/0187606 A1* | 8/2005 | Gregorich ................ | A61F 2/91 623/1.15 |
| 2005/0209678 A1 | 9/2005 | Henkes et al. | |
| 2005/0261757 A1 | 11/2005 | Shanley | |
| 2006/0155366 A1 | 7/2006 | LaDuca et al. | |
| 2006/0190075 A1 | 8/2006 | Jordan et al. | |
| 2006/0247759 A1 | 11/2006 | Burpee et al. | |
| 2006/0247761 A1 | 11/2006 | Greenberg et al. | |
| 2007/0203559 A1 | 8/2007 | Freudenthal et al. | |
| 2007/0208416 A1 | 9/2007 | Burpee et al. | |
| 2007/0276464 A1 | 11/2007 | Valencia et al. | |
| 2007/0289677 A1 | 12/2007 | Ma et al. | |
| 2008/0125855 A1 | 5/2008 | Henkes et al. | |
| 2008/0294234 A1 | 11/2008 | Hartley et al. | |
| 2009/0036976 A1 | 2/2009 | Beach et al. | |
| 2009/0082846 A1 | 3/2009 | Chobotov | |
| 2009/0216307 A1 | 8/2009 | Kaufmann et al. | |
| 2009/0216308 A1 | 8/2009 | Hartley | |
| 2009/0254165 A1 | 10/2009 | Tabor et al. | |
| 2009/0326641 A1 | 12/2009 | Davis et al. | |
| 2010/0004728 A1 | 1/2010 | Rao et al. | |
| 2010/0286760 A1 | 11/2010 | Beach et al. | |
| 2010/0292778 A1 | 11/2010 | Roeder et al. | |
| 2011/0009940 A1 | 1/2011 | Grandfield et al. | |
| 2011/0009941 A1 | 1/2011 | Grandfield et al. | |
| 2011/0009950 A1 | 1/2011 | Grandfield et al. | |
| 2011/0060212 A1 | 3/2011 | Slee et al. | |
| 2011/0106234 A1 | 5/2011 | Grandt | |
| 2011/0125252 A1 | 5/2011 | Goddard et al. | |
| 2011/0230957 A1 | 9/2011 | Bonsignore et al. | |
| 2012/0016463 A1 | 1/2012 | Ishida et al. | |
| 2012/0083868 A1 | 4/2012 | Shrivastava et al. | |
| 2012/0143237 A1 | 6/2012 | Cam et al. | |
| 2012/0245671 A1 | 9/2012 | Wainwright et al. | |
| 2012/0245672 A1* | 9/2012 | Arbefeuille ............... | A61F 2/07 623/1.13 |
| 2014/0088678 A1 | 3/2014 | Wainwright et al. | |
| 2015/0290005 A1* | 10/2015 | Wainwright ............ | A61F 2/915 623/1.12 |

FOREIGN PATENT DOCUMENTS

| | | |
|---|---|---|
| EP | 1025812 A1 | 8/2000 |
| WO | WO-03/028588 A2 | 4/2003 |
| WO | WO-2006/044147 A2 | 4/2006 |
| WO | WO-2011/53693 A1 | 5/2011 |
| WO | WO-2011/144336 | 11/2011 |

\* cited by examiner

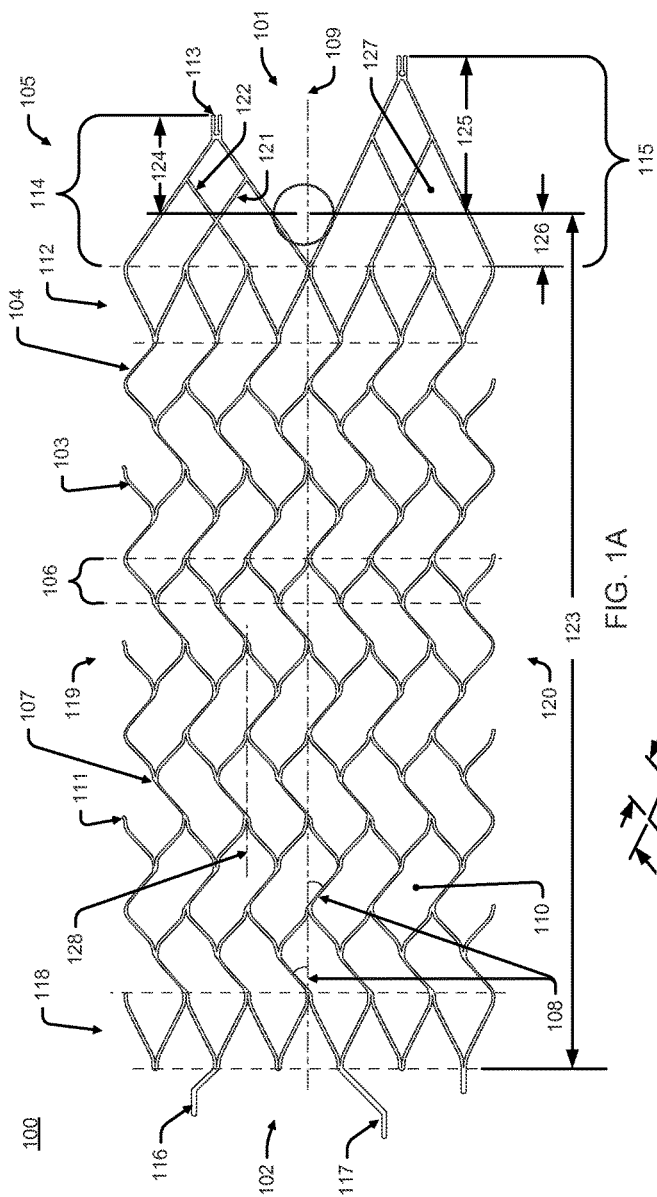
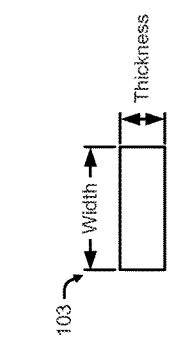
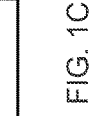

VASCULAR STENT WITH IMPROVED VESSEL WALL APPOSITION

CROSS-REFERENCES TO RELATED APPLICATIONS

The present application is a continuation of U.S. patent application Ser. No. 13/428,822, filed on Mar. 23, 2012, which claims the benefit of U.S. Provisional Patent Application Ser. No. 61/467,916, filed on Mar. 25, 2011, each of which is hereby incorporated by reference in its entirety, including Attachment A of U.S. Provisional Patent Application Ser. No. 61/467,916, for all purposes.

FIELD

The subject technology relates generally to implantable devices for interventional therapeutic treatment and, more particularly, to vascular stents with improved vessel wall apposition, e.g., for treatment of intracranial neurovascular disease.

BACKGROUND

Neurovascular (e.g., cerebral) aneurysms affect about 5% of the population. Aneurysms may be located, for example, along arterial side walls. The aneurysms may have a fundus, a neck, and a fundus-to-neck ratio or "neck ratio." If the neck ratio is greater than 2 to 1 or if the neck is less than 4 mm, the aneurysm may be treated with embolization coils alone because the coils will generally constrain themselves within the aneurysm without herniating into parent vessels. If the neck ratio is less than 2 to 1 or if the neck is greater than 4 mm, the aneurysms may be difficult to treat with embolization coils alone because the coils may be prone to herniating, or dislodging, into parent vessels. Dislodging of coils may cause arterial occlusion, stroke, and/or death.

In order to inhibit such dislodging, tubular neck remodeling devices may be used to keep coils or other materials within the fundus of the aneurysm and out of the vessels. Tubular remodeling devices generally consist of a braided wire or cut metallic stent or stents covering the neck of the aneurysm so that materials introduced into the fundus of the aneurysm do not herniate out of the aneurysm.

Moreover, occlusion of a blood vessel can be caused by a thrombus (i.e., blood clot) that forms in the blood vessel, or by an embolus, i.e., a blood clot that travels downstream. The blockage disrupts blood flow, which prevents oxygen and nutrients from being delivered to their intended locations. Tissue distal to a blood clot that is deprived of oxygen and nutrients can no longer function properly. For every minute that treatment is delayed, additional cellular death of critical tissue can occur.

Current technology for blood flow restoration, for example for treating cerebral arteries occluded by thrombi, can often take hours to reestablish flow in the artery, and can lead to unintended complications. Apparatus and methods for treating cerebral thrombi are often ineffective or only partially effective at resolving thrombus removal, and may result in distal embolization or embolization of uninvolved arteries. For example, some current devices are designed to pierce through a thrombus, or are designed to deploy distally to the thrombus before engaging the thrombus. These devices often fail to capture all of a thrombus, can damage vessel walls distal of a thrombus, can be difficult to maneuver, can unintentionally dislodge portions of a thrombus prior to capture, and/or can take significant amounts of time to restore blood flow.

Additional treatment options include endovascular therapy and/or pharmacological agents. Pharmacological agents, specifically thrombolytics, can be used to dissolve a thrombus and restore blood flow. However, these drugs often do not work in recanalizing the vessel, may not be suitable for some patients, and may take an extended length of time to work, which can impact the cellular death distal of the thrombus. Often these drugs are used within a short treatment window, and patients late in presentation are not eligible for drug treatment. Also, these drugs can increase the risk of hemmorhage.

SUMMARY

There have been numerous problems in the use of stents and vasooclusive devices within the vasculature of the human body. Some devices ovalize when placed in a tortuous lumen. This may also be referred to as "kinking" or "fish mouthing." Other devices may herniate into an aneurysm. This problem may be referred to as "gator-backing", "I shelfing", and "ledge effect". Some devices abruptly move distally, or "jump," during the last portion of stent deployment. This may cause the proximal portion of the stent to protrude into the aneurysm also known as "ice cream cone" if the length is not oversized. Consequently, stents are often seen as having thrombogenic properties. Due to the need to use anticoagulants with such stents, few doctors have been known to be comfortable using such stents to treat a ruptured aneurysm. In some instances, an aneurysm may be ballooned and coiled, and then a stent is placed several weeks later to minimize the thrombogenic effect. It is also unknown how many aneurysms could be treated using a form of flow diversion. Furthermore, visibility of stents under fluoroscopy is often difficult, and the trackability of stents in the vasculature has not been optimal.

The stent of the subject technology solves some or all of the foregoing problems by providing a vessel-engaging stent designed for bridging the neck of aneurysms that may be fully retrieved, even when fully deployed for unmatched procedural control.

The subject technology is illustrated, for example, according to various aspects described below. Various examples of aspects of the subject technology are described as numbered clauses (1, 2, 3, etc.) for convenience. These are provided as examples, and do not limit the subject technology. It is noted that any of the dependent clauses may be combined in any combination, and placed into a respective independent clause, e.g., clause 1, 20, 32, and 50. The other clauses can be presented in a similar manner.

1. A medical device, comprising:
    a delivery wire having a proximal end and a distal end;
    a connection mechanism; and
    a vessel-engaging member attached to the distal end of the delivery wire via the connection mechanism, the vessel-engaging member comprising:
    a plurality of rows, each row having a plurality of struts arranged in an alternating pattern such that for each row, a first set of vertices is positioned on a proximal side, and a second set of vertices is positioned on a distal side;
    a plurality of bridges positioned between each adjacent row, each of the bridges connecting a vertex of a first row with a corresponding vertex of a second row, each bridge having a bridge length and an angle relative to a longitudinal axis of the member; and first and second tapered sections coupled to the connection mechanism, each of the tapered sections projecting from a proximal row and tapering in a direction from the proximal row toward the connection mechanism, each of the tapered sections having a length measured along the longitudinal axis;

wherein the length of the first tapered section is less than the length of the second tapered section.

2. The medical device of clause 1, wherein the vertex of the first row lies substantially along a line parallel to the longitudinal axis of the member and the vertex of the second row lies outside the line.

3. The medical device of clause 1, wherein each of the plurality of struts has a strut length, and wherein the strut length is greater than the bridge length.

4. The medical device of clause 1, wherein each of the plurality of struts has a strut length, and wherein the strut length and the bridge length is the same.

5. The medical device of clause 1, wherein a cross-sectional width of each of the plurality of bridges is less than a cross-sectional width of each of the struts to which that bridge connects.

6. The medical device of clause 1, wherein the first tapered section comprises a first and second connecting member with distal ends connected to the proximal row and distal ends connected to the first tapered section.

7. The medical device of clause 6, wherein the first and second connecting members intersect.

8. The medical device of clause 1, wherein the first tapered section is connected to the proximal row at a middle vertex and a first strut endpoint, and the second tapered section is connected to the proximal row at the middle vertex and a second strut endpoint.

9. The medical device of clause 1, wherein the device has a working region and a first and second non-working region, each region having a length, the working region comprising the plurality of rows and a portion of the tapered sections, the first non-working region comprising a remaining portion of the first tapered section, the second non-working region comprising a remaining portion of the second tapered section.

10. The medical device of clause 9, wherein the length of the first non-working region is less than the length of the second non-working region.

11. The medical device of clause 1, wherein the distal end of the delivery wire comprises a first connection wire and a second connection wire, wherein the first connection wire is releasably connected to the first tapered section via the connection mechanism, and the second connection wire is releasably connected to the second tapered section via the connection mechanism.

12. A method of implanting a medical device in the neurovasculature comprising:
inserting a guide catheter into the neurovasculature;
inserting a microcatheter through the distal end of the guide catheter;
inserting a vessel-engaging member into the microcatheter such that the distal portion of the member is located adjacent a treatment site in the neurovasculature, wherein the member comprises:
a plurality of rows, each row having a plurality of struts arranged in an alternating pattern such that for each row, a first set of vertices is positioned on a proximal side and a second set of vertices is positioned on a distal side;
a plurality of bridges positioned between each adjacent row, each of the bridges connecting a vertex of a first row with a corresponding vertex of a second row, each bridge having a bridge length and an angle relative to a longitudinal axis of the member; and
first and second tapered sections projecting from a proximal row and tapering in a direction from the proximal row toward a proximal end of the member, each of the tapered sections having a length measured along the longitudinal axis;
wherein the length of the first tapered section is less than the length of the second tapered section; and
withdrawing the microcatheter so as to expose and deploy the vessel-engaging member, the vessel-engaging member configured to expand against and engage the treatment site.

13. The method of clause 12, further comprising retrieving the vessel-engaging member by moving the microcatheter until the microcatheter covers a portion of the vessel-engaging member, and then withdrawing both the microcatheter and vessel-engaging member together proximally.

14. The method of clause 12, wherein expanding against and engaging the treatment site comprises extending the vessel-engaging member across a neck of an aneurysm, wherein the vessel-engaging member acts as a scaffolding to inhibit herniation of objects out of the neck of the aneurysm.

15. The method of clause 14, further comprising inserting embolic material into a fundus of the aneurysm.

16. The method of clause 15, wherein inserting embolic material comprises inserting embolic coils.

17. The method of clause 12, further comprising detaching the vessel-engaging member via a connection mechanism.

18. The method of clause 17, further comprising repositioning the vessel-engaging member prior to detachment.

19. The method of clause 12, wherein the treatment site comprises a lumen with tortuous curvature.

20. A method of implanting a medical device in a lumen at a tortuous curve, comprising:
inserting a vessel-engaging member into the lumen, the member comprising:
a plurality of rows, each row having a plurality of struts arranged in an alternating pattern such that for each row, a first set of vertices is positioned on a proximal side and a second set of vertices is positioned on a distal side;
a plurality of bridges positioned between each adjacent row, each of the bridges connecting a vertex of a first row with a corresponding vertex of a second row, each bridge having a bridge length and an angle relative to a longitudinal axis of the member; and
first and second tapered sections projecting from a proximal row and tapering in a direction from the proximal row toward a proximal end of the member, each of the tapered sections having a length measured along the longitudinal axis;
wherein the length of the first tapered section is less than the length of the second tapered section; and
contacting a wall of the lumen with the member at an apex of the tortuous curve by deflecting the plurality of bridges adjacent to the apex so that vertices adjacent to the deflecting the plurality of bridges contact the wall of the lumen.

21. A medical device, comprising:
   a delivery wire having a proximal end and a distal end;
   a connection mechanism; and
   a vessel-engaging member attached to the distal end of the delivery wire via the connection mechanism, the vessel-engaging member comprising:
      a plurality of strut rows, each row having a plurality of struts arranged in an alternating pattern such that for each row, a first set of vertices is positioned on a proximal side, and a second set of vertices is positioned on a distal side;
      a plurality of bridges positioned between each adjacent row, each of the bridges connecting a vertex of a first row with a corresponding vertex of a second row, each bridge having a bridge length and an angle relative to a longitudinal axis of the member such that the vertex of the first row lies substantially along a line with vertices of at least two other rows that are adjacent to each other; and
      first and second tapered sections coupled to the connection mechanism, each of the tapered sections projecting from a proximal strut row and tapering in a direction from the proximal row toward the connection mechanism;
      wherein the vertex of the second row lies substantially outside the line.
22. The medical device of clause 21, wherein the vertex of the first row and the vertices of the at least two other rows all lie on either the proximal or distal side of their respective rows.
23. The medical device of clause 21, wherein each of the plurality of struts has a strut length, and wherein a ratio of the bridge length to the strut length is at least approximately 0.30.
24. The medical device of clause 21, wherein each of the plurality of struts has a strut length, and wherein a ratio of the bridge length to the strut length is at least approximately 0.40.
25. The medical device of clause 21, wherein each of the plurality of struts has a strut length, and wherein a ratio of the bridge length to the strut length is at least approximately 0.50.
26. The medical device of clause 21, wherein each of the plurality of struts has a strut length, and wherein a ratio of the bridge length to the strut length is at least approximately 0.60.
27. The medical device of clause 21, wherein each of the plurality of struts has a strut length, and wherein a ratio of the bridge length to the strut length is at least approximately 0.70.
28. The medical device of clause 21, wherein each of the plurality of struts has a strut length, and wherein a ratio of the bridge length to the strut length is at least approximately 0.80.
29. The medical device of clause 21, wherein each of the plurality of struts has a strut length, and wherein a ratio of the bridge length to the strut length is at least approximately 0.90.
30. The medical device of clause 21, wherein each of the plurality of struts has a strut length, and wherein a ratio of the bridge length to the strut length is at least approximately 1.0.
31. The medical device of clause 21, wherein the vessel-engaging member is modifiable into a volume-reduced having a generally coiled, tubular configuration for insertion within a microcatheter, an edge of a distal portion of the member being overlapped in the volume-reduced coiled configuration such that in the volume-reduced coiled configuration the vessel-engaging member has multiple layers in at least one radial direction.
32. The medical device of clause 21, wherein a cross-sectional width of each of the plurality of bridges is less than a cross-sectional width of each of the struts to which that bridge connects.
33. The medical device of clause 32, wherein the cross-sectional width of each of the plurality of bridges is approximately 0.05 mm and the cross-sectional width of each of the plurality of struts is approximately 0.055 mm.
34. The medical device of clause 32, wherein a region at the vertex of each of the plurality of struts has a cross-sectional width of approximately 0.065 mm.
35. The medical device of clause 32, wherein the bridge length is approximately 1.5 mm, and each of the plurality of struts has a strut length of approximately 2 mm.
36. The medical device of clause 32, wherein the bridge length is approximately 1.5 mm, and each of the plurality of struts has a strut length of approximately 1.75 mm.
37. The medical device of clause 21, wherein the first tapered section is connected to the proximal strut row at a middle vertex and a first strut endpoint, and the second tapered section is connected to the proximal row at the middle vertex and a second strut endpoint.
38. The medical device of clause 21, wherein the first tapered section is shorter than the second tapered section, in the direction of the longitudinal axis.
39. The medical device of clause 21, wherein the distal end of the delivery wire comprises a first connection wire and a second connection wire, wherein the first connection wire is releasably connected to the first tapered section via the connection mechanism, and the second connection wire is releasably connected to the second tapered section via the connection mechanism.
40. An implantable device, comprising:
   a plurality of strut rows, each row having a plurality of struts arranged in an alternating pattern such that for each row a first set of vertices is positioned on a proximal side, and a second set of vertices is positioned on a distal side;
   a plurality of bridges positioned between each adjacent row, each of the bridges connecting a vertex of a first row with a corresponding vertex of a second row, each bridge having a bridge length and an angle relative to a longitudinal axis of the member such that the vertex of the first row lies substantially along a line with vertices of at least two other rows that are adjacent to each other; and
   first and second tapered sections projecting from a proximal strut row and tapering in a direction from the proximal row toward a distal end of the device;
   wherein the vertex of the second row lies substantially outside the line.
41. The medical device of clause 40, wherein the vertex of the first row and the vertices of the at least two other rows all lie on either the proximal or distal side of their respective rows.
42. The medical device of clause 40, wherein each of the plurality of struts has a strut length, and wherein a ratio of the bridge length to the strut length is at least approximately 0.30.

43. The medical device of clause 40, wherein each of the plurality of struts has a strut length, and wherein a ratio of the bridge length to the strut length is at least approximately 0.40.
44. The medical device of clause 40, wherein each of the plurality of struts has a strut length, and wherein a ratio of the bridge length to the strut length is at least approximately 0.50.
45. The medical device of clause 40, wherein each of the plurality of struts has a strut length, and wherein a ratio of the bridge length to the strut length is at least approximately 0.60.
46. The medical device of clause 40, wherein each of the plurality of struts has a strut length, and wherein a ratio of the bridge length to the strut length is at least approximately 0.70.
47. The medical device of clause 40, wherein each of the plurality of struts has a strut length, and wherein a ratio of the bridge length to the strut length is at least approximately 0.80.
48. The medical device of clause 40, wherein each of the plurality of struts has a strut length, and wherein a ratio of the bridge length to the strut length is at least approximately 0.90.
49. The medical device of clause 40, wherein each of the plurality of struts has a strut length, and wherein a ratio of the bridge length to the strut length is at least approximately 1.0.
50. The medical device of clause 40, wherein the cross-sectional width of each of the plurality of bridges is approximately 0.05 mm and the cross-sectional width of each of the plurality of struts is approximately 0.055 mm, and wherein the bridge length is approximately 1.5 mm, and each of the plurality of struts has a strut length of approximately 1.75 mm.
51. The medical device of clause 40, wherein the first tapered section is shorter than the second tapered section, in the direction of the longitudinal axis, and wherein the distal end of the delivery wire comprises a first connection wire and a second connection wire, wherein the first connection wire is releasably connected to the first tapered section via the connection mechanism, and the second connection wire is releasably connected to the second tapered section via the connection mechanism.
52. A method of implanting a medical device in the neurovasculature comprising:
    inserting a guide catheter into the neurovasculature;
    inserting a microcatheter through the distal end of the guide catheter;
    inserting a vessel-engaging member into the microcatheter such that the distal portion of the member is located adjacent a treatment site in the neurovasculature, wherein the member comprises:
    a plurality of strut rows, each row having a plurality of struts arranged in an alternating pattern such that for each row, a first set of vertices is positioned on a proximal side and a second set of vertices is positioned on a distal side;
    a plurality of bridges positioned between each adjacent row, each of the bridges connecting a vertex of a first row with a corresponding vertex of a second row, each bridge having a bridge length and an angle relative to a longitudinal axis of the member such that the vertex of the first row lies substantially along a line with vertices of at least two other rows that are adjacent to each other; and
    first and second tapered sections projecting from a proximal strut row and tapering in a direction from the proximal row toward a distal end of the member;
    wherein the vertex of the second row lies substantially outside the line; and
    withdrawing the microcatheter so as to expose and deploy the vessel-engaging member, the vessel-engaging member configured to expand against and engage the treatment site.
53. The medical device of clause 52, wherein the vertex of the first row and the vertices of the at least two other rows all lie on either the proximal or distal side of their respective rows.
54. The method of clause 52, wherein each of the plurality of struts has a strut length, and wherein a ratio of the bridge length to the strut length is at least approximately 0.30.
55. The method of clause 52, wherein each of the plurality of struts has a strut length, and wherein a ratio of the bridge length to the strut length is at least approximately 0.40.
56. The method of clause 52, wherein each of the plurality of struts has a strut length, and wherein a ratio of the bridge length to the strut length is at least approximately 0.50.
57. The method of clause 52, wherein each of the plurality of struts has a strut length, and wherein a ratio of the bridge length to the strut length is at least approximately 0.60.
58. The method of clause 52, wherein each of the plurality of struts has a strut length, and wherein a ratio of the bridge length to the strut length is at least approximately 0.70.
59. The method of clause 52, wherein each of the plurality of struts has a strut length, and wherein a ratio of the bridge length to the strut length is at least approximately 0.80.
60. The method of clause 52, wherein each of the plurality of struts has a strut length, and wherein a ratio of the bridge length to the strut length is at least approximately 0.90.
61. The method of clause 52, wherein each of the plurality of struts has a strut length, and wherein a ratio of the bridge length to the strut length is at least approximately 1.0.
62. The method of clause 52, further comprising retrieving the vessel-engaging member by moving the microcatheter until the microcatheter covers a portion of the vessel-engaging member, and then withdrawing both the microcatheter and vessel-engaging member together proximally.
63. The method of clause 52, wherein expanding against and engaging the treatment site comprises expanding against a length of a thrombus and engaging a thrombus, the method further comprising:
    retrieving the thrombus by moving the microcatheter until the microcatheter covers a portion of the vessel-engaging member, and then withdrawing both the microcatheter and vessel-engaging member together proximally.
64. The method of clause 63, further comprising providing aspiration through a balloon guide catheter to assist in removing the thrombus.
65. The method of clause 63, further comprising withdrawing the thrombus at least partially into the microcatheter.

66. The method of clause 52, further comprising detaching the vessel-engaging member via a connection mechanism.
67. The method of clause 52, further comprising repositioning the vessel-engaging member prior to detachment.
68. The method of clause 52, wherein the treatment site comprises a stenosis.
69. The method of clause 52, wherein the treatment site comprises an aneurysm.
70. A medical device comprising:
    a vessel-engaging member that engages a wall of a blood vessel, the member comprising:
    a plurality of strut rows, each row having a plurality of struts arranged in an alternating pattern such that for each row, a first set of vertices is positioned on a proximal side, and a second set of vertices is positioned on a distal side; and
    a plurality of bridges positioned between each adjacent row, each of the bridges connecting a vertex of a first row with a corresponding vertex of a second row, each bridge having a bridge length and an angle relative to a longitudinal axis of the member such that the vertex of the first row lies substantially along a line with vertices of at least two other rows that are adjacent to each other;
    wherein the vertex of the second row lies substantially outside the line;
    wherein each of the plurality of struts has a strut length, and wherein a ratio of the bridge length to the strut length is at least 0.30.
71. The medical device of clause 70, wherein the vertex of the first row and the vertices of the at least two other rows all lie on either the proximal or distal side of their respective rows.
72. The medical device of clause 70, wherein the ratio of the bridge length to the strut length is at least 0.40.
73. The medical device of clause 70, wherein the ratio of the bridge length to the strut length is at least 0.50.
74. The medical device of clause 70, wherein the ratio of the bridge length to the strut length is at least 0.60.
75. The medical device of clause 70, wherein the ratio of the bridge length to the strut length is at least 0.70.
76. The medical device of clause 70, wherein the ratio of the bridge length to the strut length is at least 0.80.
77. The medical device of clause 70, wherein the ratio of the bridge length to the strut length is at least 0.90.
78. The medical device of clause 70, wherein the ratio of the bridge length to the strut length is at least 1.0.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

A detailed description will be made with reference to the accompanying drawings:

FIG. 1A depicts an implantable device comprised of struts, bridges, and two tapered protrusions at a proximal end of the implant according to one aspect of the subject technology.
FIG. 1B depicts a perspective view of a strut according to one aspect of the subject technology.
FIG. 1C depicts a cross-sectional view of a strut according to one aspect of the subject technology.

DETAILED DESCRIPTION

Figure 2:
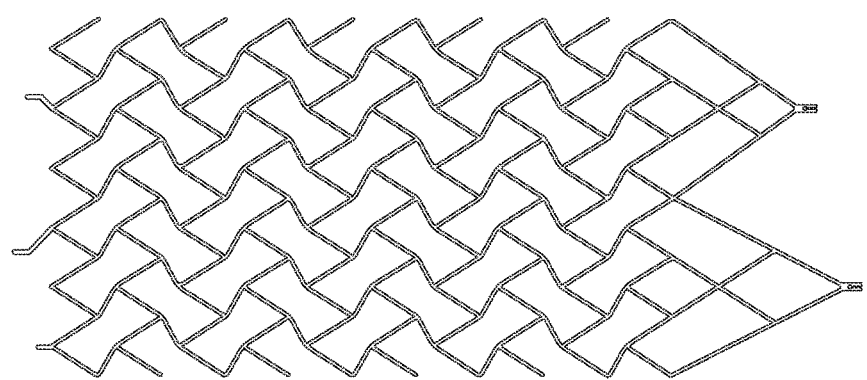
FIG. 2 depicts an implantable device including a shorter bridge length according to one aspect of the subject technology.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology.

There have been numerous problems in the use of stents and vasoocclusive devices within the vasculature of the human body. Some devices ovalize when placed in a tortuous lumen. This may also be referred to as "kinking" or "fish mouthing." Other devices may herniate into an aneurysm. This problem may be referred to as "gator-backing", "I shelfing", and "ledge effect". Some devices abruptly move distally, or "jump," during the last portion of stent deployment. This may cause the proximal portion of the stent to protrude into the aneurysm also known as "ice cream cone" if the length is not oversized. Consequently, stents are often seen as having thrombogenic properties. Due to the need to use anticoagulants with such stents, few doctors have been known to be comfortable using such stents to treat a ruptured aneurysm. In some instances, an aneurysm may be ballooned and coiled, and then a stent is placed several weeks later to minimize the thrombogenic effect. It is also unknown how many aneurysms could be treated using a form of flow diversion. Furthermore, visibility of stents under fluoroscopy is often difficult, and the trackability of stents in the vasculature has not been optimal.

The stent of the subject technology solves some or all of the foregoing problems by providing a vessel-engaging stent designed for bridging the neck of aneurysms that may be fully retrieved, even when fully deployed for unmatched procedural control.

The vessel-engaging member may extend across the neck of the aneurysm and act as a scaffolding to inhibit or prevent herniation or prolapse of objects (e.g., embolization coils, thrombi, etc.) out of the neck of the aneurysm. The vessel-engaging member may allow insertion of embolic material therethrough. The embolization coils may be a single embolization coil or other embolic material (e.g., embolic fluid).

The embolization coils or other embolic material may be inserted into a fundus of the aneurysm before or after positioning and deployment of the vessel-engaging member in the vessel. In some embodiments, the embolization coils are inserted in the fundus of the aneurysm using the same catheter from which the vessel-engaging member is deployed. In some embodiments, the embolization coils are inserted in the fundus of the aneurysm using a different catheter than the catheter from which the vessel-engaging member is deployed. In certain such embodiments, a guidewire may be used to guide both catheters.

The vessel-engaging stent may engage a wall of the vessel utilizing various suitable means. For example, the vessel-engaging stent may be a self-expanding stent and/or a balloon-expandable stent. In some aspects, "vessel" may refer to blood vessels (including arteries and veins) or other suitable body organs having a lumen, such as the gastrointestinal tract (e.g., esophagus, stomach, small intestine, colon, rectum), bile ducts, urinary bladder, ureter, urethra, trachea, bronchi, and the like. As will be seen below the device is designed such that a fully-deployed circumference of the device more uniformly tracks a vessel lumen, even in tortuous curvatures. The bridge-strut configuration of the subject technology improves wall apposition, coil support, trackability, deployment accuracy, and radiopacity.

FIG. 1A depicts an implantable device including struts and bridges according to one aspect of the subject technology. As depicted by FIG. 1A, the implantable device 100 includes a proximal end 101 and a distal end 102, and may be comprised of struts 103 and bridges 104. The device may further include two tapered protrusions 105 at the proximal end 101 of the device for connecting device 100 to a delivery wire. The implantable device 100 is shown cut longitudinally and laid flat. The device may include rows 106 of struts joined together at their vertices 107 by a plurality of bridges 104. While nine rows 106 of struts 103 are illustrated in FIG. 1A, it is understood that any number greater than two rows of struts are suitable for the disclosure. As shown by FIG. 1A, the struts 103 of each row 106 may be alternatively positioned at a substantially ninety degree angle relative to each other in a zigzag-like pattern. Each vertex 107 (or bend point) is connected by a bridge 104 to a corresponding vertex of an adjacent row of struts. In one aspect, each row 106 is mirrored and laterally shifted relative to the row at the opposite end of a connecting bridge, such that the vertices connected by the bridge are facing each other, inward toward the bridge. A strut 103 and bridge 104 may be aligned such that the bridge angle 108 from the longitudinal axis 109 of the device may be approximately 45 degrees.

As depicted by FIG. 1A, the bridge length and angle may be set such to maintain the strut vertices substantially inline. Thus, while each bridge connects a mirrored vertex 107, the vertices of the rows 106 may appear to be oriented in the same direction. The configuration and arrangement of struts 103 and bridges 104 creates a matrix of cells 110 over the surface of the device. It has been found that, in the subject technology, the larger the bridge angle 108, the better the retractability of the device. However, at larger angles (for example, over fifty degrees) the size of the cells 110 created by the configuration increases such that vessel wall support may begin to decline. Therefore, in some aspects, the bridge angle 108 may be set between ten and fifty degrees. The angle used, however, is not limited to any specific value. An angle of greater than fifty degrees or less than ten degrees may also be used without deviating from the scope of the subject technology. In some aspects, the implantable device 100 is configured such that an inscribed circle diameter of, for example, 1.7 mm may fit within each cell 110 when the implantable device 100 has a cross-sectional diameter of 4 mm. In some aspects, the implantable device may have a cross-sectional diameter of between 2 and 6 mm. However, other suitable cross-sectional diameters may be used without deviating from the scope of the subject technology.

In some aspects, the device of the subject technology may be dimensioned to include a radius of approximately 4 mm in a deployed state, or less than or equal to 4 mm. As depicted by FIG. 1A, each row 106 may include twelve struts, each strut alternating direction in a zigzag pattern. In one aspect, the strut tips 111 (for example, at each alternating vertex in a row) may be arranged to be substantially inline. In some aspects, the distal strut tips and vertices may be inline with other distal strut tips and vertices. In some aspects, the proximal strut tips and vertices may be inline with other proximal strut tips and vertices. For example, as one proceeds from row to row, the vertices on the proximal sides of the rows are inline with each other, and the vertices on the distal sides of the rows are inline with each other. In some aspects, the sets of proximal and distal vertices are laterally shifted with respect to each other, e.g., with a given proximal vertex laterally midway between an adjacent pair of distal vertices, and vice versa. For example, the proximal vertices may lay substantially along a line 128 parallel to the longitudinal axis 109 and the distal vertices may lay outside the line 128. The strut length may, for example, be selected to be 1.8 mm and set off from each other at approximately ninety degrees to form a device with a radius of approximately 4 mm. Other strut lengths may be selected without departing from the scope of the technology. For example, the strut lengths may also be selected to be shorter to create more points to bend as the strut is flexed longitudinally and/or compressed or flexed at its diameter. In the depicted example, bridge length is selected to be approximately 1.5 mm. As with strut lengths, the bridge length may be varied to be shorter or longer than 1.5 mm without departing from the scope of the invention. As will be described below, the ratio of bridge length to strut length may impact certain characteristics of the device and/or vary the number of bridges or struts that may be used to implement the various aspects of the subject technology.

According to certain aspects, the ratio of the bridge length to the strut length may be optimized to increase wall apposition of implantable device 100, especially when implantable device 100 has to bend (e.g., when placed in a curved area). In some aspects, the ratio of the bridge length to the strut length may be at least approximately 0.30. In some aspects, the ratio of the bridge length to the strut length may be at least approximately 0.40. In some aspects, the ratio of the bridge length to the strut length may be at least approximately 0.50. In some aspects, the ratio of the bridge length to the strut length may be at least approximately 0.60. In some aspects, the ratio of the bridge length to the strut length may be at least approximately 0.70. In some aspects, the ratio of the bridge length to the strut length may be at least approximately 0.80. In some aspects, the ratio of the bridge length to the strut length may be at least approximately 0.90. In some aspects, the ratio of the bridge length to the strut length may be at least approximately 1.0. The ratio of the bridge length to the strut length may be other suitable values that may increase wall apposition.

Figure 7:
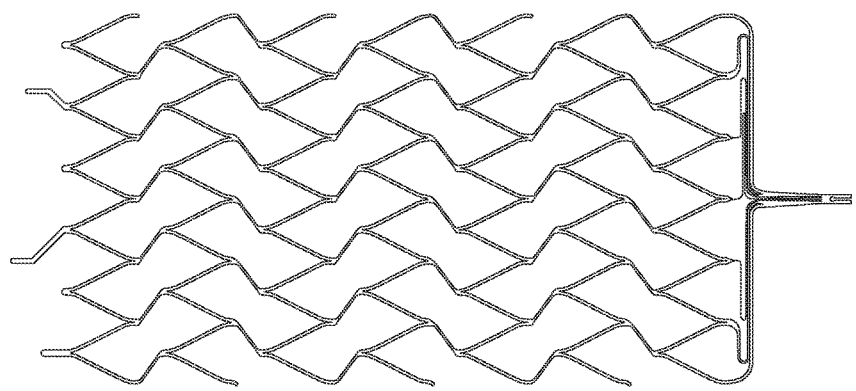
FIG. 7 depicts an implantable device including a first compact single tip design according to one aspect of the subject technology.

Turning briefly to FIG. 7, an implantable device including a longer strut length is shown according to one aspect of the subject technology. As depicted, the length of the struts may be increased (relative to bridge length) and the angle of the struts may be decreased (for example, to between thirty and sixty degrees) to maintain the desired diameter of the device. In one example, the strut length may be 2 mm. Other strut lengths and angles may be selected in a similar manner to maintain a diameter size, or may be adjusted accordingly to other selected radii (for example, a diameter less than 4 mm or greater than 4 mm).

Turning back to FIG. 1A, the bridges connecting the vertices of alternating rows of struts may be selected to be thinner in width relative to the struts. For example, a strut width may be selected to be approximately 0.055 mm to provide sufficient radial support when the device is deployed in a lumen. In contrast, a width of the bridges may be selected to be approximately 0.050 mm. Accordingly, the subject technology may include a thinner bridge width to enhance longitudinal flexibility, and provide better arching capability. When deployed in a tortuous lumen, the device of the subject technology will be more likely to bend at a bridge 104 location than at a strut 103 location, as may be the case in other technologies, thus providing improved wall apposition at a curve.

Figure 14:
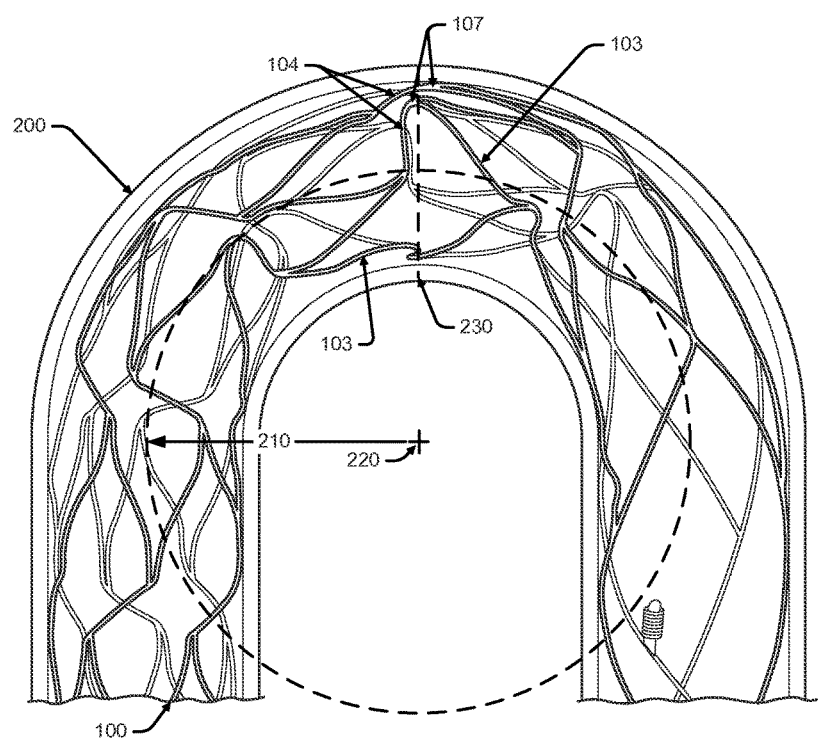
FIG. 14 is a photographic representation of a side view of an implantable device in a tortuous lumen according to one aspect of the subject technology.
Figure 15:
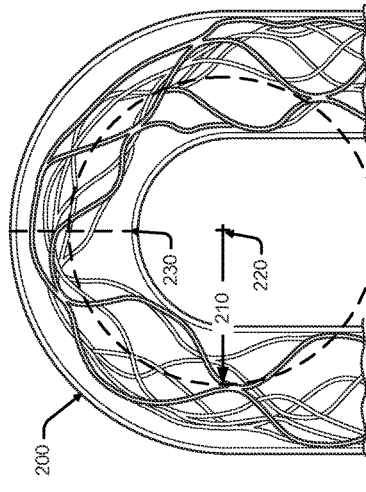
FIG. 15 is a photographic representation of a side view of a prior art device in a tortuous lumen.
Figure 16:
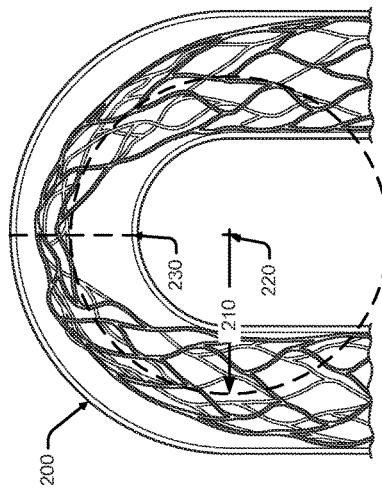
FIG. 16 is a photographic representation of a side view of a prior art device in a tortuous lumen.
Figure 17:
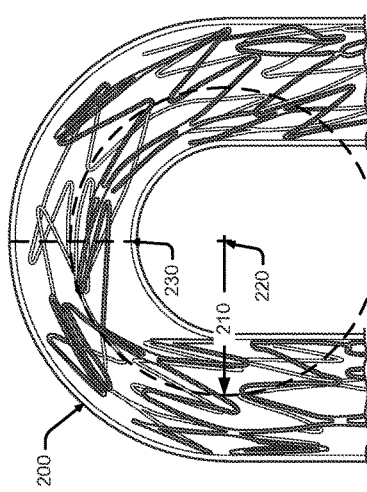
FIG. 17 is a photographic representation of a side view of a prior art device in a tortuous lumen.
Figure 18:
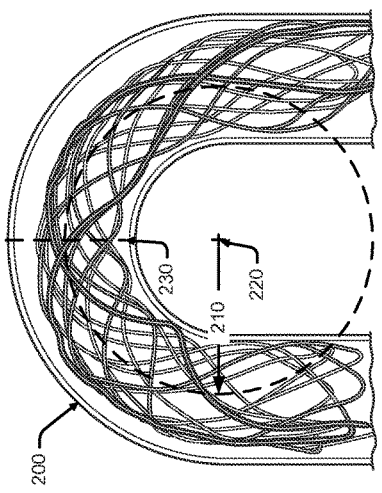
FIG. 18 is a photographic representation of a side view of a prior art device in a tortuous lumen.

For example, referring to FIG. 14, the device 100 is disposed in a vessel 200 with tortuous curvature. The vessel 200 may have a diameter of about 3 mm and may include a curve with a center point 220, having a radius 210 of about 3.9 mm. The curve may have an apex 230 located at a midpoint of the curve. The apex may also represent a peak of the curve, or a point on the curve equidistant from endpoints of the curve. At the apex 230, the bridges 104 adjacent the apex 230 are deflected to allow the vertices 107 adjacent to the deflecting bridges to contact an inner surface of the vessel or lumen, thereby providing improved wall apposition near the apex 230. In one aspect, a distance between strut rows 106 disposed adjacent to the deflecting bridges is less than a distance between strut rows disposed away from the deflecting bridges. The reduced distance between the strut rows may cause the vertices 107 adjacent to the apex 230 to be near each other. In some aspects, by allowing the vertices 107 to move near each other, the vertices 107 may better conform to the shape of the curve. In contrast, referring to FIGS. 15-18, prior art devices deployed in the tortuous vessel 200 ovalize, kink, or fish mouth, when placed in the tortuous lumen. Accordingly, the prior art devices do not provide satisfactory wall apposition in a tortuous lumen.

FIG. 1B depicts a perspective view of a strut 103 according to one aspect of the subject technology. FIG. 1C depicts a cross-sectional view of the strut 103 according to one aspect of the subject technology. As shown, the strut 103 has a rectangular cross-section. In some aspects, a bridge 104 may have a similar rectangular cross-section. However, the strut 103 and the bridge 104 may have other suitable cross-sectional shapes, such as an elliptical cross-section (e.g., circular) or a polygonal cross-section.

In some aspects, a strut width at the tip of the strut may be sized slightly larger than its width. For example, wherein a strut width of 0.055 is selected, a tip width of approximately 0.065 mm may be selected. The increased strength resulting from the increased width of the tips may enhance durability of the device, for example, during deployment or retraction of the device from the deploying micro-catheter. In further aspects, one or more strut tip widths may be reduced to distribute strain on the device when deployed in certain tortuous configurations. It has been found that the configuration depicted in FIG. 2 produces a peak strain of approximately 7.8% during crimping.

In one aspect, the device may have 24 struts in a row, each having a length of approximately 1 mm, and a width of between approximately 0.03 and 0.10 mm. In this aspect, the bridge length may be approximately 0.2 mm, and have a bridge width of between approximately 0.025 and 0.095 mm. In this aspect, the bridge angle from the longitudinal axis of the device may be approximately 0 degrees. In a second aspect, the device may have 8 struts in a row, each having a length of approximately 3 mm, and a width of between approximately 0.03 and 0.10 mm. In this aspect, the bridge length may be approximately 3 mm, and have a bridge width of between approximately 0.025 and 0.095 mm. In this aspect, the bridge angle from the longitudinal axis of the device may be approximately 90 degrees. In a third aspect, the device may have 12 struts in a row, each having a length of approximately 2 mm, and a width of approximately 0.065 mm. In this aspect, the bridge length may be approximately 1.5 mm, and have a bridge width of approximately 0.045 mm. In this aspect, the bridge angle from the longitudinal axis of the device may be approximately 50 degrees.

As depicted by FIG. 1A, the device may also include one or more tapered sections 105 protruding from a proximal row 112 of struts. In one aspect, the struts of the proximal (and/or distal) row may be selected to be longer than 1.8 mm and set off from each other at less than ninety degrees (for example, between approximately forty-five to sixty degrees). A proximal row 112 may include five vertices and two opposing end points (for example, strut tips 111) on the proximal side. These vertices may be used for connecting the primary, workable structure of the device to the one or more tapered sections 105. For example, each tapered section 105 may extend from three of these vertices and one end point of the proximal row 112, with each tapered section sharing an intermediate-positioned vertex. Each tapered section may include a V shaped structure extending from the outer most end points (strut tips 111), and an X shaped structure within and supporting the V shaped structure, extending from the inner most vertices of proximal row 112. For example, a first and second connecting member, 121 and 122 respectively, may extend from the inner most vertices of proximal row 112 to the tapered section 105. The first and second connecting members, 121 and 122 respectively, may intersect thereby forming the X. The proximal end point of each tapered section (vertex of the V shaped structure) may further include a connection point 113 for detachable connection to a delivery wire. Each delivery wire connection point 113 (and/or vertex of the V shaped structure) may be constructed from a radiopaque material or include a radiopaque marker allowing in vivo imaging of the stent.

Figure 19:
FIG. 19 is a side view of an implantable device according to one aspect of the subject technology.
Figure 20:
FIG. 20 is a side view of an implantable device according to one aspect of the subject technology.
Figure 21:
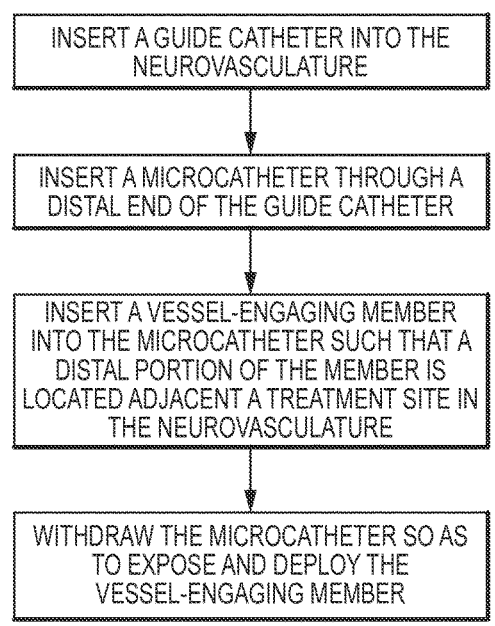
FIG. 21 illustrates a method according to one aspect of the subject technology.

Each tapered section 105 may have a length measured along the longitudinal axis. In some aspects, the length of one of the tapered sections may be less than the length of another tapered section. For example, as depicted by FIG. 1A, the device may have a working, or active, region 123 configured to perform a medical procedure and a first and second non-working, or inactive, region, 124 and 125 respectively. Each region may have a length. The working region 123 may comprise the plurality of rows 106 and a portion 126 of the tapered sections 105. The first non-working region 124 may comprise a remaining portion of a first tapered section 114. The second non-working region 125 may comprise a remaining portion of a second tapered section 113. In one aspect, to minimize thrombogenic effects, the length of the tapered sections 105 should be minimized. Accordingly, the first non-working region 124 may have a length of ranging from about 3.3 mm to about 2.6 mm and the second non-working region 125 may have a length ranging from about 5.3 mm to about 4.6 mm. In some aspects, the difference in length between the tapered sections allows the connection points 113 to be aligned with one another when the implantable device 100 collapses (e.g., when the implantable device 100 is stowed as opposed to being deployed). In some aspects, each delivery wire connection point may be connected to a distal end of a delivery wire, such that when the device is fully deployed, the longer tapered section may fold down toward the shorter tapered section, creating a tapered proximal end. In another aspect, the distal end of the delivery wire may split (for example, as depicted by FIGS. 19 and 20).

In one aspect, the tapered sections 105 allows the delivery wire to act directly on the device via the shorter tapered section 114, with the longer tapered section 115 providing stability and control. In this regard, the tapered sections 105 and complete circular design of the device in its deployed state may improve trackability, and may act to minimize retrieval forces, minimize the non-working length, improve pushability, and the like. For example, the device 100 may have a delivery or pushability force of less than 1.4 N (Newton), such as 1.17 N. The device 100 may also have a retrieval force of less than 2 N, such as 0.9 N. When fully expanded, the improved wall apposition enabled by the subject technology may also work to minimize thrombogenic effects. In some aspects, a non-thrombogenic coating may further be applied to the device to further reduce the thrombogenicity of the device.

When deployed, the tapered sections 105 may conform to the shape of the device inside the lumen, and become rigidly fixed outward longitudinally from the device. In some aspects, the device may also include at a distal end one or more open extending distal tips 116, 117. These distal tips 116 may extend from corresponding bridges that protrude from a distal row 118 of struts. In FIG. 1A, for example, the device is shown with a first distal tip 116 and a second distal tip 117, each extending from a bridge connected to a distal vertex of the distal row, and a third distal tip directly extending from a third vertex 107 of the distal row 118. In some aspects, one of the distal tips may be longer than the other or may extend out further via a longer bridge connection. When the device is fully deployed, the farthest protruding tip may fold down toward and connect to the shorter protruding tip to provide a narrow and/or tapered profile at the distal end of the device. Thus, when deployed, the device may be more navigable than if the distal tips were not connected. Alternatively, the distal tips may be in an unconnected configuration and/or configured to separate during or after deployment of the device.

In some aspects, the distal tips may include "hook-like" elements for ensnaring, capturing, and/or gripping portions of a thrombus. For example, it has been found that using the configuration of the distal tips illustrated in the distal end 102 of FIG. 1A may be useful in retrieving thrombi. In particular, it has been found that in aspects where there are three or four such distal tips along the end of the vessel-engaging element, the distal tips themselves may be able to capture a thrombus and/or help with thrombus retention during retrieval of the thrombus. Because the distal tips may protrude inward slightly from the rest of the vessel-engaging member, the thrombus may adhere to the shape of the distal tips. In some aspects the distal tips may be staggered both circumferentially and longitudinally along the distal end 102 of the vessel-engaging member. The staggered placement of distal tips may allow the thrombus to adhere to multiple distal tips, for example at different locations along the length of the thrombus.

The distal tips may include, for example, a platinum distal marker band. As a marker band, the distal element may be used during an imaging process to identify a location or locations of the vessel-engaging member during a blood flow restoration procedure.

Figure 3:
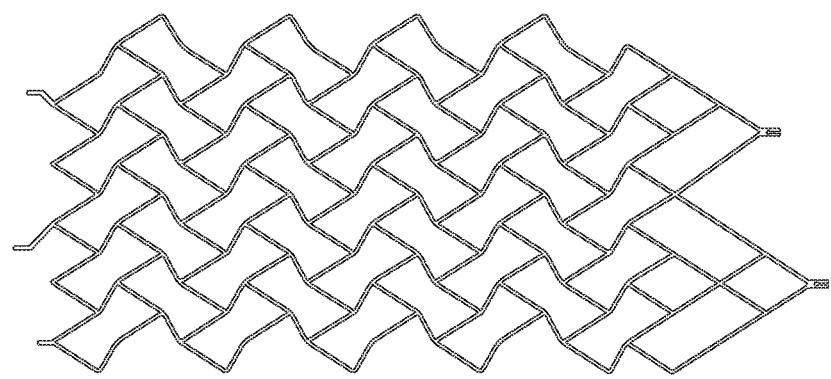
FIG. 3 depicts an implantable device including a longitudinal split design and tapered sections of a reduced size according to one aspect of the subject technology.
Figure 4:
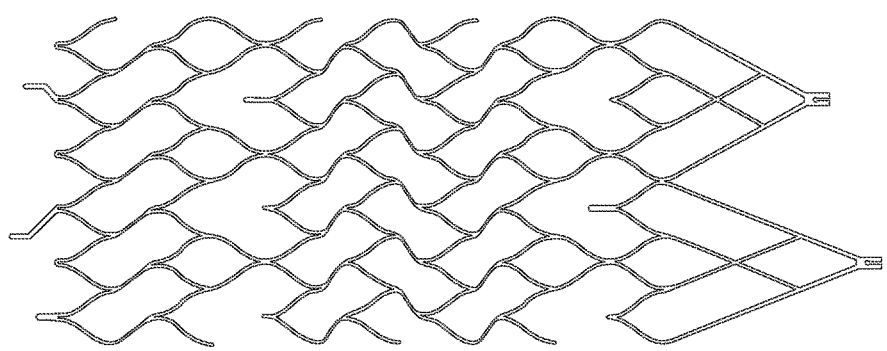
FIG. 4 depicts an implantable device including tapered struts in a modular strut pattern according to one aspect of the subject technology.
Figure 5:
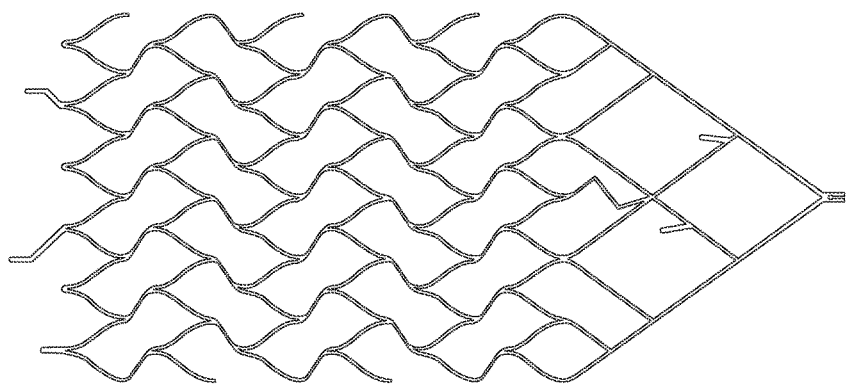
FIG. 5 depicts an implantable device including tapered struts in a uniform strut pattern according to one aspect of the subject technology.
Figure 6:
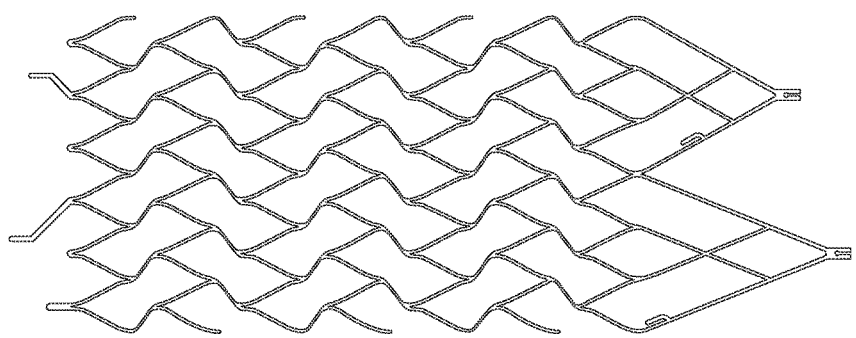
FIG. 6 depicts an implantable device including longer struts in combination with shorter bridges according to one aspect of the subject technology.
Figure 8:
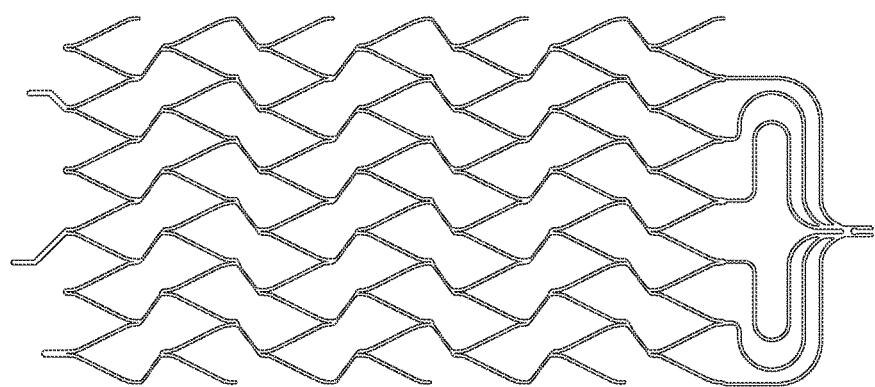
FIG. 8 depicts an implantable device including a second compact single tip design according to one aspect of the subject technology.
Figure 9:
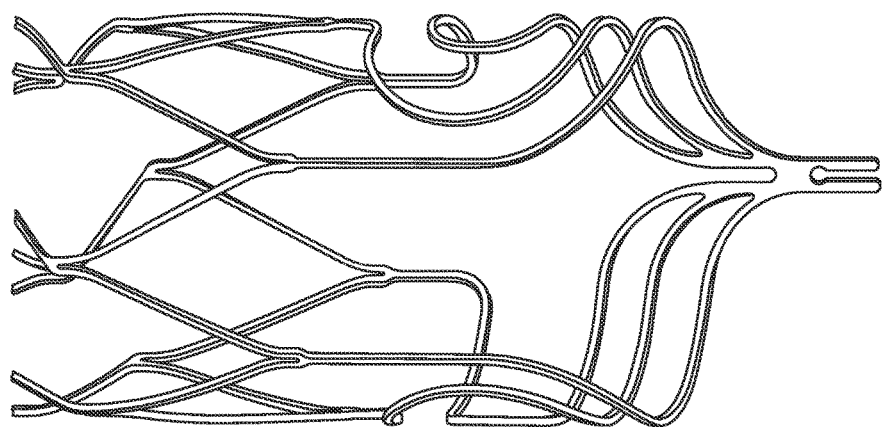
FIG. 9 depicts a deployed configuration of an implantable device including a second compact single tip design according to one aspect of the subject technology.
Figure 10:
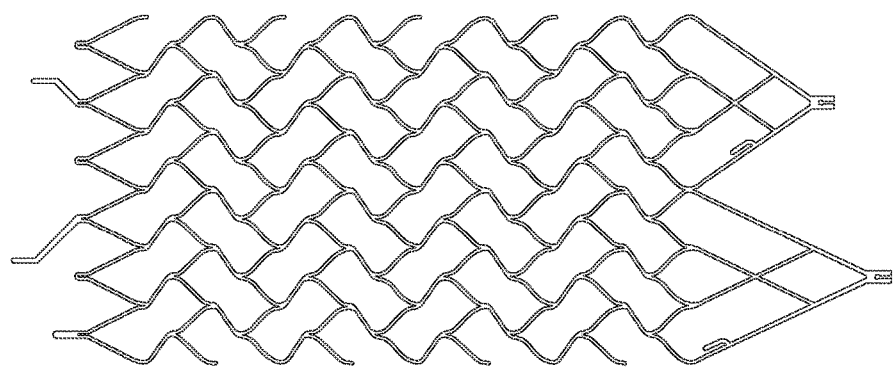
FIG. 10 depicts an implantable device including eight equal rows of tapered struts and one distal row of longer struts according to one aspect of the subject technology.
Figure 11:
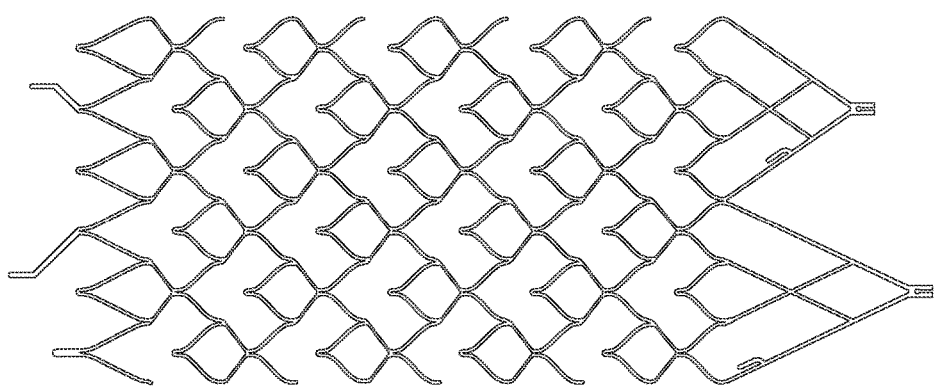
FIG. 11 depicts an implantable device including an alternating bridge pattern according to one aspect of the subject technology.

Other strut-bridge configurations are further disclosed in the accompanying figures. FIG. 2 depicts an implantable device including a shorter bridge length according to one aspect of the subject technology. FIG. 3 depicts an implantable device including a longitudinal split design and tapered sections of a reduced size according to one aspect of the subject technology. FIG. 4 depicts an implantable device including S-shaped struts in a modular strut pattern according to one aspect of the subject technology. FIG. 5 depicts an implantable device including S-shaped struts in a uniform strut pattern according to one aspect of the subject technology. FIG. 6 depicts an implantable device including longer struts in combination with shorter bridges according to one aspect of the subject technology. FIG. 7 depicts an implantable device including a first longitudinally compact single tip design according to one aspect of the subject technology. FIG. 8 depicts an implantable device including a second longitudinally compact single tip design according to one aspect of the subject technology. FIG. 9 depicts a deployed configuration of an implantable device including a second longitudinally compact single tip design according to one aspect of the subject technology. FIG. 10 depicts an implantable device including eight equal rows of S-shaped struts and one distal row of longer, straighter struts according to one aspect of the subject technology. FIG. 11 depicts an implantable device including an alternating bridge pattern according to one aspect of the subject technology.

Other aspects and figures of the subject technology may be found in the specification and drawings of co-pending application Ser. No. 12/896,707, entitled "Methods and Apparatuses for Flow Restoration and Implanting Members in the Human Body," filed Oct. 1, 2010, application Ser. No. 61/420,275, entitled "Vascular Remodeling Device," filed Dec. 6, 2010, and application Ser. No. 61/448,506, entitled "Vascular Remodeling Device," filed Mar. 2, 2010, which are all incorporated by reference in their entirety for all purposes.

The struts and bridge configuration of the vessel-engaging member (for example, device 100) may be formed, for example, by laser cutting a pre-formed tube or sheet by interconnecting a multitude of filaments by laser welding, or by other suitable methods. In one aspect, the vessel-engaging member is initially laser cut from a tube, such that a longitudinal slit (that is, cut) along a length of the device is present. In alternative aspects, the vessel-engaging member may be formed by cutting a pattern of struts, bridges, etc., on a flat sheet and then rolling the flat sheet into a generally tube-like or coiled shape. Other methods for forming the vessel-engaging member are also possible.

In one arrangement, the vessel-engaging member may be formed from alloys having shape-memory properties, such as NITINOLO, though other materials are also possible. In some aspects the vessel-engaging member may be subjected to a tempering treatment at temperatures customarily applied to the material so that the impressed structure is permanently established.

The vessel-engaging member may have various lengths and diameters. In some aspects, the vessel-engaging member may have lengths, measured proximally to distally along the longitudinal axis 109, ranging from 15 mm to 40 mm, though other ranges and sizes are also possible. The vessel-engaging member may also have specific diameters, the diameters being measured when the vessel-engaging member is fully free to expand. In some aspects, the vessel-engaging member may have a diameter of between approximately 3 mm and 4 mm so as to be used in size 18 microcatheters (i.e., microcatheters with an inner diameter of approximately 0.21 inch). In some aspects the vessel-engaging member may have a diameter of between approximately 5 mm and 6 mm so as to be used in size 27 microcatheters (i.e., microcatheters with an inner diameter of approximately 0.027 inch). Other ranges and values are also possible.

In some aspects, the vessel-engaging member may include a plurality of individual filaments (for example, struts 103 and/or bridges 104) and individual cells 110, as well as a first edge 119 and a second edge 120. In other aspects, the first edge 119 and the second edge 120 may be connected to each other to form a substantially cylindrical shape by welding, soldering, or otherwise joining the strut tips 111 of the first edge 119 with the strut tips 111 of the second edge.

In another aspect, the first edge and second edge may be formed, for example, from cutting a preformed, etched tube longitudinally along the length of the tube. The vessel-engaging member may be curled such that edges 119 and 120 overlap one another when the vessel-engaging member is in a volume-reduced form. While in a volume-reduced form, the vessel-engaging member, similar to a wire mesh roll, or piece of paper, may be curled up such that it may be introduced into a microcatheter and moved within the microcatheter. The vessel-engaging member may have a central longitudinal axis while in both a volume-reduce form and when fully or partially expanded. Upon release from the microcatheter, the curled-up vessel-engaging member may spring open and attempt to assume a fully expanded shape. Upon expansion, the vessel-engaging member may expand towards an inner wall of a vessel, or towards a thrombus occluding the inner wall of a vessel. The extent of any overlap of the vessel-engaging member within the vessel after expansion may be governed by the vessel size. For example, in narrower vessels a greater overlap of the edges 119 and 120 may occur, whereas in wider vessels the overlap may be smaller, or even an "underlap" may occur, in which case the edges 119 and 120 are separated by an open gap or space within the vessel. In some aspects, when the vessel-engaging member is collapsed, the struts become parallel with one another. In some aspects, the vessel-engaging member is circumferentially compressed.

Figure 12:
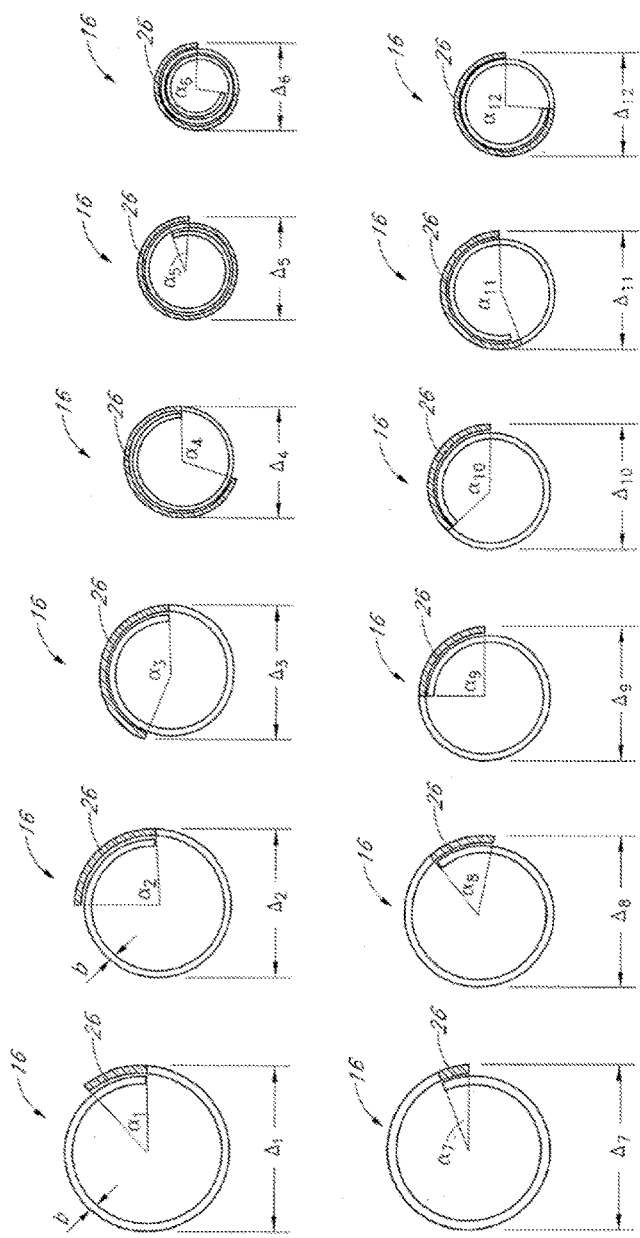
FIG. 12 is a schematic illustration of overlap configurations of a vessel-engaging implantable device as seen from a distal end according to one aspect of the subject technology.
Figure 13:
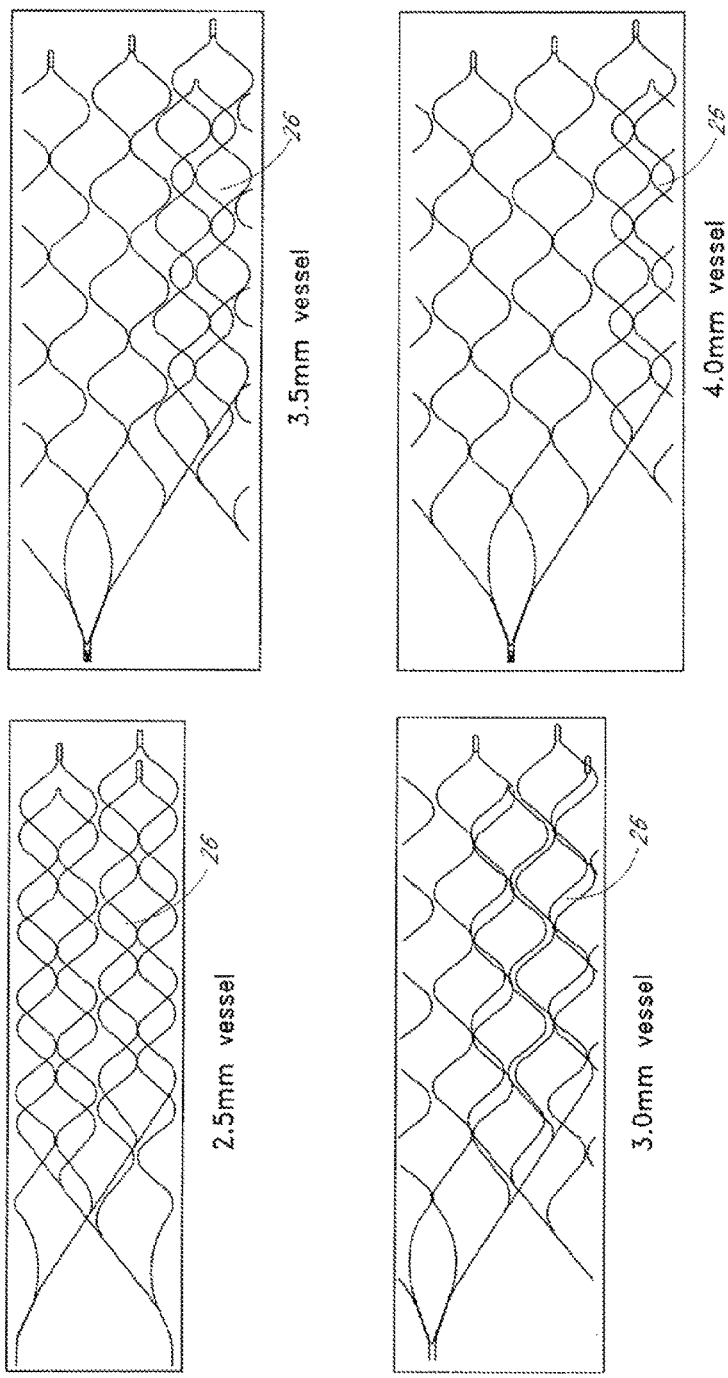
FIG. 13 is a schematic illustration of overlap configurations of a vessel-engaging implantable device as seen from a side elevational view according to one aspect of the subject technology.

FIG. 12 is a schematic illustration of overlap configurations of a vessel-engaging implantable device as seen from a distal end according to one aspect of the subject technology. In one aspect, the vessel-engaging member may experience various degrees of overlap in a volume-reduced form, forming zones of overlap 26. The vessel-engaging member may assume various diameters $\Delta_1$, $\Delta_2$, etc., depending on the degree of the overlap (e.g. represented by angle $\alpha_1$, $\alpha_2$, etc.). FIG. 13 is a schematic illustration of overlap configurations of a vessel-engaging implantable device as seen from a side elevational view according to one aspect of the subject technology. As illustrated in FIG. 13, the overlap zones 26 may vary in size and configuration depending on the vessel size. When inside a vessel, the overlap zone 26 of the vessel-engaging member may advantageously provide grip and/or retaining ability with respect to a thrombus. For example, when the vessel-engaging member expands against a thrombus, the individual filaments (for example, struts 103 and/or bridges 104) and individual cells 110 of the overlap zone 26 may embed into and grip, or retain, the thrombus. The overlap zone 26 may provide added grip or retention due to the fact that there are multiple layers of filaments, in a radial direction, that act to grip or retain the thrombus. Thus, instead of just one layer of filaments embedding into the thrombus, the overlap zone 26 may include two or more layers of filaments that embed into the thrombus. The overlap zone 26 may prove particularly useful when attempting to remove a thrombus, since the layers of filaments (for example, struts 103 and/or bridges 104) may inhibit the thrombus from slipping and/or sliding away from the vessel-engaging member.

Additionally, where the vessel-engaging member has a longitudinal slit, or other type of slit (e.g. a slit at an angle relative to a longitudinal axis of the vessel-engaging member), the cells 110 may advantageously retain their general shape upon expansion. For example, while the vessel-engaging device is expanding within a vessel, the cells 110 may generally retain the shape illustrated in, for example, FIG. 1A, due to the fact that the first and second edges are free to move relative to one another. Without a slit, or open tube design, the shape of the individual cells 110 could tend to distort, (e.g. narrow or widen), as the vessel-engaging device expands and contracts. This change in shape of the individual cells 110 may disadvantageously cause the vessel-engaging device to lose its grip on the thrombus. This change in shape may also disadvantageously cause the individual cells 110 to "pinch" off portions of the thrombus as the cells 110 change shape, thus allowing thrombus debris (e.g. small pieces of the thrombus) to escape and raise the likelihood of clots developing further downstream.

In some aspects, the vessel-engaging member may include a proximal portion and a distal portion. As illustrated by, for example, FIGS. 1A through 4, the proximal portion may include one or more taper sections 105. In some aspects, the taper sections 105 may have individual cells 127 that have a different size than the individual cells 110. For example, in some aspects, the taper sections 105 may have individual cells 127 that have a size larger than that of the individual cells 110. Each taper section 105 may taper gradually towards a connection mechanism 113, or some other connection point along the device 100 that connects the vessel-engaging member to a delivery wire. For example, in some aspects the connection mechanism 113 may include a generally non-detachable interface or transition point between the vessel-engaging member and the delivery wire. In some aspects the connection mechanism 113 may be integrally formed with the delivery wire and/or vessel-engaging member. In some aspects connection mechanisms 113 may include a releasable connection mechanism for easily releasing the device 100. For the purposes of this disclosure, the subject technology may use a delivery wire and/or a pushwire without limitation. In this regard, the term delivery wire may refer to what one skilled in the art may call a pushwire and vice versa. Therefore, for simplicity, the terms delivery wire and pushwire are used interchangeably.

Depending on the procedure and intended use of the vessel-engaging member, it may be advantageous to have a connection mechanism 113 that permits release of the vessel-engaging member. For example, during a blood flow restoration procedure, it may prove difficult and/or dangerous to fully retrieve a thrombus due to a complicated vasculature or the risk of damaging a vessel wall. Leaving the vessel-engaging member behind may prove to be the only option available to a surgeon or other medical personnel. In other circumstances the vessel-engaging member may include drug-eluding capabilities, and/or may be coated with a particular type of drug that facilitates thrombus dissolution. It may be advantageous in such circumstances to release the vessel-engaging member and allow the vessel-engaging member to anchor the thrombus against the vessel wall while the thrombus is dissolved by the drug. Various types of materials, drugs, and/or coatings for a vessel-engaging member are described, for example, in International Application Publication No. WO 2009/105710.

Connection mechanism 113 may include, for example, an electrolytically severable region. While other types of connection mechanisms are also possible (e.g. a purely mechanical connection or a connection that involves heating and melting a connection area), in one aspect, the connection mechanism 113 comprises a connection that dissolves under the influence of electrical energy when in contact with an electrolyte. The electrolytically severable region may include an exposed piece of electrolytically severable material, such as stainless steel, though other materials are also possible. The electrolytically severable region may be coated with a strengthening material, such as parylene, though other types of coating material are also possible. In some aspects, the electrolytically severable region may include a portion of the delivery wire. In one aspect, the length of the electrolytically severable region may range from 0.1 mm to 0.5 mm, and more preferable from 0.2 mm to 0.4 mm, though other ranges and values are also possible.

In one aspect, the connection mechanism 113 may further comprise a stem with a ball located at a distal end of the stem. The stem and/or ball may be coated with insulative material and/or adhesive, to inhibit or prevent electric current from traveling through the connection mechanism to the vessel-engaging member. The connection mechanism may further comprise a keyway structure. The keyway structure may include a slit and/or opening that is configured to receive the stem and/or ball, and to lock the stem and/or ball in place. In some aspects, the keyway structure may include part of proximal portion of the vessel-engaging member. In some aspects the keyway structure may include NITINOLO, though other materials are also possible. The connection mechanism 113 may further comprise a sleeve. The sleeve may surround the keyway structure, stem, and/or ball. The sleeve may be comprised of platinum, though other materials are also possible. The sleeve may include, for example, a proximal radiopaque marker. The connection mechanism may further comprise a shrink tubing surrounding a distal delivery wire section. In some aspects the distal delivery wire section may include a coil. Similar to the severable region, the distal delivery wire section may be coated with parylene, though other materials are also possible.

Overall, the structure of connection mechanism 113 may be configured such that the vessel-engaging member releases at a predetermined point. For example, the vessel-engaging member may generally be isolated from electric current, such that during detachment of the vessel-engaging member, only the electrolytically severable region disintegrates in blood, and the vessel-engaging member separates from the delivery wire cleanly at the electrolytically severable region, and is released into the vessel.

Other aspects and types of connection mechanisms 113 are also possible. For example, connection mechanism 113 may include a dumb-bell shaped element that dissolves under the influence of electrical energy when in contact with an electrolyte. At the proximal (i.e., delivery wire side) end of the dumb-bell shaped element, a spiral structure may interact with a strengthening spiral of the delivery wire. At the distal end, a ball-shaped element may be arranged that, with the help of a laser welding technique, is connected to a platinum spiral which, in turn, is linked with a connection point situated at a proximal end of the vessel-engaging member. In some aspect the platinum spiral may serve as an X-ray reflecting proximal marker of the vessel-engaging member. To strengthen the joint between the ball-shaped element and the connection point, a reinforcement wire may be provided. Alternatively, the platinum spiral may also be designed to withstand tensile and thrust forces imposed upon it. The dumb-bell shaped separating element may include a steel material that is susceptible to corrosion in an electrolyte under the influence of electrical energy. To accelerate corrosion and shorten the separating time span, a structural or chemical weakening of the dumb-bell shaped element may be beneficial, for example, by applying grinding methods or thermal treatment. In some aspects, the portion of the dumb-bell shaped element accessible to the electrolyte has a length of 0.1 mm to 0.5 mm, particularly 0.3 mm, though other ranges and values are also possible. The spiral structure may be secured via welding both to the dumb-bell shaped element and the reinforcement spiral of the delivery wire. The delivery wire itself may be slidably accommodated within the microcatheter. In some aspects the dumb-bell shaped element may have a ball-shaped element at each end. The ball shaped elements may be connected distally to the connection point of the vessel-engaging member and proximally to the delivery wire via spirals, respectively.

The taper sections 105 of proximal portion may be at various angles relative to the delivery wire. In some aspects, the taper sections 105 may advantageously facilitate retraction and repositioning of the device. In some aspects, the taper sections 105 may also be designed to generally not contact the vessel wall during a blood flow restoration procedure, and to generally not interfere with the flow of blood within a vessel. For example, in some aspects generally only the distal portion of the device, and its individual struts 103 and individual cells 110, contact a vessel wall and/or thrombus.

The vessel-engaging device may be designed to engage and remove thrombi that are both generally soft, or malleable, or generally hard, or callous. In one aspect, the vessel-engaging member described above, however, may advantageously be designed to engage both soft and hard thrombi of varying thickness and location. For example, the vessel-engaging member may be designed to have specific strut lengths, widths, and thicknesses, such that the vessel-engaging member is optimally configured to engage and remove a wide range of thrombi.

The individual cells 110 of the vessel-engaging member may also be designed and sized such that the vessel-engaging member is optimally configured to engage and remove a wide range of thrombi. For example, in one aspect, the individual cells 110 of the vessel-engaging member may have an area of between 2.85 mm$^2$ and 7.83 mm$^2$. The cell area and/or inscribed circle diameter may vary depending on the configuration of struts 103 and bridges 104, and vessel diameter of the device. For example, a device having a mesh pattern similar to FIG. 5 and a vessel diameter of 2 mm may include a cell area of approximately 2.85 mm$^2$ and an inscribed circle diameter of approximately 0.96 mm. A device having a mesh pattern similar to FIG. 5 and a vessel diameter of 3 mm may include a cell area of approximately 4.73 mm$^2$ and an inscribed circle diameter of approximately 1.42 mm. A device having a mesh pattern similar to FIG. 5 and a vessel diameter of 4 mm may include a cell area of approximately 5.23 mm$^2$ and an inscribed circle diameter of approximately 1.45 mm. A device having a mesh pattern similar to FIG. 5 and a vessel diameter of 5 mm may include a cell area of approximately 6.78 mm$^2$ and an inscribed circle diameter of approximately 1.97 mm. A device having a mesh pattern similar to FIG. 6 and a vessel diameter of 2 mm may include a cell area of approximately 3.06 mm$^2$ and an inscribed circle diameter of approximately 0.92 mm. A device having a mesh pattern similar to FIG. 6 and a vessel diameter of 3 mm may include a cell area of approximately 5.58 mm$^2$ and an inscribed circle diameter of approximately 1.5 mm. A device having a mesh pattern similar to FIG. 6 and a vessel diameter of 4 mm may include a cell area of approximately 6.27 mm$^2$ and an inscribed circle diameter of approximately 1.78 mm. A device having a mesh pattern similar to FIG. 6 and a vessel diameter of 5 mm may include a cell area of approximately 7.83 mm$^2$ and an inscribed circle diameter of approximately 2.05 mm. In some aspects, the cell sizes may vary, as may the individual filament thicknesses and widths within the proximal and/or distal portions of the device. In one example, a vessel-engaging member with a generally large cell size may provide for high circumferential conformity, flexibility, and axial rigidity, thereby promoting capture and removal of a wide range of thrombi.

In another aspect, the relationship between the total strut and bridge length of the vessel-engaging member and the total length of the thrombus to be removed may help determine whether the vessel-engaging member is optimally configured to engage and remove a particular sized thrombus. For example, the total strut and bridge length may be found by measuring the total available strut and bridge length exposed to the thrombus length using a program such as SolidWorks. The total available strut and bridge length is equivalent to the combined total lengths of all the struts and bridges in the distal portion of the vessel-engaging member or that portion of the vessel-engaging member that is generally exposed to the thrombus. The total thrombus length may be found, for example, by crossing a thrombus with a microcatheter and injecting contrast agent through the microcatheter distally of the thrombus, and then injecting contrast agent through a guide catheter proximally of the thrombus, so as to visualize and measure the length of the thrombus.

The vessel-engaging member may further be designed to generate specific forces once it is deployed and released from a microcatheter in order to optimally engage and remove a wide range of both soft and hard thrombi. By deploying the vessel-engaging member across a thrombus, the vessel-engaging member may self-expand to a larger diameter due to elastic energy stored in the vessel-engaging member. The vessel-engaging member may expand in the vessel until equilibrium is reached between the stored elastic energy and an opposing force from the surrounding vessel wall and/or thrombus. The struts, bridges and cells of the vessel-engaging member may penetrate a thrombus, promoting adhesion and embedment of the thrombus to the vessel-engaging member, and the expanding force of the vessel-engaging member may promote dislodgment of the thrombus from the vessel wall.

For example, the stored elastic energy of the vessel-engaging member may generate outward forces known as radial force (RF) and chronic outward force (COF). The radial force is equivalent to the outward force exerted by the vessel-engaging member during compression of the vessel-engaging member. The chronic outward force is equivalent to the outward force exerted by the vessel-engaging member during decompression, or expansion, of the vessel-engaging member. In one aspect, the COF may be designed so that it is not so high that it bursts, or damages, a vessel wall. In some aspects, the vessel-engaging member may be designed such that its linear force measurement is proportional to and/or equal to: $[(\text{strut width})^3/(\text{strut length})^3] \times (\text{number of struts around the circumference})$. In some aspects, the linear force measurement is proportional to and/or equal to: $[(\text{Young's modulus}) \times (\text{the angle of bend between two struts sharing a vertex}) \times (\text{strut width})^3 \times (\text{strut thickness})]/(\text{strut length})^3$. Thus, if both the strut width and the strut length are varied by the same degree, the overall linear force may stay about the same. In some aspects, the RF may be designed so that it is high enough to resist compression forces from the surrounding vessel environment, maintain patency of the vessel lumen, and restore flow through the thrombus site.

During deployment and thrombus retrieval, the highest COF and RF may occur when the vessel-engaging member is deployed and/or retrieved inside a minimum recommended diameter vessel. Conversely, the COF and RF may be the lowest when the vessel-engaging member is deployed and/or retrieved inside a maximum recommended diameter vessel. The curled, overlap nature of the vessel-engaging member may enhance the COF and RF, particularly in smaller diameter vessels, to allow for increased embedment of a thrombus to the vessel-engaging member.

By considering such factors including but not limited to anatomy, physiological environment, blood vessel mechanical properties, flow properties, pressures, stresses, and strains, methods have been developed to determine optimal radial and chronic outward forces for the vessel-engaging member.

The vessel-engaging member may have a radial force measurement greater than or equal to 0.0010 N per mm of length of the portion of the vessel-engaging member that is configured to contact a vessel wall or thrombus. The length in this unit refers to a proximal to distal direction measurement. The vessel-engaging member may have a chronic outward force of less than or equal to 0.026 N per mm of length of the portion of the vessel-engaging member that is configured to contact a vessel wall or thrombus. In one aspect, the vessel-engaging member may have a radial force measurement of between approximately 6 to 37 gf per inch of length of the portion of the vessel-engaging member that is configured to contact a vessel wall or thrombus.

By considering such factors including but not limited to anatomy, physiological environment, blood vessel mechanical properties, flow properties, pressures, stresses, and strains, methods have also been developed to determine optimal dislodgment forces for the vessel-engaging member. The dislodgment force is the force required to cause a fully deployed vessel-engaging member to slip axially along a vessel (e.g. artery) wall. Determining a lower bound dislodgment force may help ensure that the vessel-engaging member may withstand its physiological environment (e.g. forces due to blood flow and shear stress) without dislodgment from its deployed location. Determining an upper bound dislodgment force may help to evaluate the ability of the vessel to withstand retrieval of the vessel-engaging member and device 10 without causing unintended dissection or damage to the vessel wall. A dislodgment testing method, for example, may include measuring the force required to cause a fully deployed vessel-engaging member to slip axially along an in vitro model simulating an artery by pulling the device along a specified length in the tubing and recording the force at which slippage occurs. The dislodgment test comprises pulling the vessel-engaging member once along a specified length through a section of tubing and recording the force at which slippage occurs. In one aspect, the vessel-engaging member may have a dislodgment force that ranges between 0.010 N and 0.700 N, though other ranges and values are also possible.

Additionally, while the vessel-engaging member described above has been described in the context of use during a blood flow restoration procedure, the vessel-engaging member may also, or alternatively, be used as an implantable member (e.g. stent). For example, the vessel-engaging member may be released through the connection mechanism at a stenosis, aneurysm, or other appropriate location in a vessel. The vessel-engaging member may expand and engage a vessel wall so as to hold the vessel wall open and/or act as an occluding member. While the strut thicknesses, widths, cell sizes, and forces described above may be optimized for a vessel-engaging member designed for flow restoration, these values may also be optimized for a vessel-engaging member designed for use as an implantable member. In some aspects they are the same values.

In some aspects the vessel-engaging member may be designed specifically for use as a flow restoration device and/or an implantable member (e.g. stent) at a bifurcation, bi-vessel, and/or multi-vessel. For example, thrombi may be located at bifurcations in the neurovasculature such as the internal carotid artery and the anterior cerebral artery, or internal carotid artery and middle cerebral artery, or the basilar artery and the posterior cerebral artery. Thrombi may also be located at two vessels (i.e., bi-vessels) as two separate clots in similar vessels. Thrombi may also be located at multi-vessels as one clot that is within multiple vessels or as multiple clots that are within multiple vessels. Vessels with such clots may be located, for example, at the intracranial internal carotid, anterior cerebral and middle cerebral arteries, and basilar artery and both posterior and cerebral arteries.

The vessel-engaging member may have shapes and/or sizes that accommodate the types of vessel and clots. For example, the vessel-engaging member may have a proximal portion similar to proximal portion described above. The vessel-engaging member may further have a distal portion that is divided into two or more branches. The branches may be designed specifically, for example, for different types of bifurcations and splits commonly found in the neurovasculature. Similar to the distal portion described above, the distal portion may be configured to expand against a thrombus or vessel wall. At least a portion of the vessel-engaging member may be slit and/or cut.

While aspects of the device 100 have been described herein, various other aspects of the device may be found, for example, in U.S. Pat. No. 7,300,458, U.S. Patent Publication No. 2008/0125855, and PCT Publication No. WO 2009/105710, each of which is incorporated by reference in its entirety.

Turning back to FIG. 1A, radiopaque markers may be located adjacent the proximal or distal ends 101, 102 or both, and may be located at any position along the length of the device between the proximal and distal stent ends 101, 102. In one aspect, the markers may be located at or on connection points 113 and/or distal tips 116 and 117. The markers may be attached to implant 100 by techniques such as adhesives, heat fusion, interference fit, fasteners, intermediate members, as coatings, or by other techniques. In one aspect, the markers are comprised of radiopaque materials press fit into a through-hole provided in a tab. It will be appreciated that other shapes and other interlock configurations could also be used. International Application Publication No. WO 2009/105710, entitled, "Methods and Apparatus for Flow Restoration," filed on Feb. 20, 2009, which is incorporated by reference in its entirety, describes various uses of marker bands and imaging of a vessel-engaging member.

In some aspects, the markers are comprised of ultrasonic markers, MRI safe markers, or other markers. In one aspect ultrasonic markers permit a physician to accurately determine the position of device 100 within a patient under ultrasonic visualization. Ultrasonic visualization is especially useful for visualizing device 100 during non-invasive follow-up and monitoring. Materials for ultrasonic marker have an acoustical density sufficiently different from device 100 to provide suitable visualization via ultrasonic techniques. Exemplary materials comprise polymers (for metallic stents), metals such as tantalum, platinum, gold, tungsten and alloys of such metals (for polymeric or ceramic stents), hollow glass spheres or microspheres, and other materials.

In some aspects, MRI safe markers permit a physician to accurately determine the position of device 100 within a patient under magnetic resonance imaging. MRI visualization is especially useful for visualizing device 100 during non-invasive follow-up and monitoring. Exemplary materials for making MRI safe marker have a magnetic signature sufficiently different from device 100 to provide suitable visualization via MRI techniques. Exemplary materials comprise polymers (for metallic stents), metals such as tantalum, platinum, gold, tungsten and alloys of such metals (for polymeric or ceramic stents), non-ferrous materials, and other materials.

In further aspects, device 100 may be comprised of metal, polymer, ceramic, permanent enduring materials, and may comprise either of or both of non-bioabsorbable and bioabsorbable materials. Exemplary materials include but are not limited to Nitinol, stainless steel, cobalt chromium alloys, Elgiloy, magnesium alloys, polylactic acid, poly glycolic acid, poly ester amide (PEA), poly ester urethane (PEU), amino acid based bioanalogous polymers, tungsten, tantalum, platinum, polymers, bio-polymers, ceramics, bio-ceramics, or metallic glasses. Part or all of implant 10 may elute over time substances such as drugs, biologics, gene therapies, antithrombotics, coagulants, anti-inflammatory drugs, immunomodulator drugs, anti-proliferatives, migration inhibitors, extracellular matrix modulators, healing promoters, re-endothelialization promoters, or other materials. In some aspects, device 100 may be comprised of shape memory urethane polymer. Device 100 may be manufactured by forming cells 110 through the wall of the tube, by means such as laser cutting, electrochemical etching, grinding, piercing, or other means. In some aspects device 100 is formed by electroforming. In one aspect, device 100 may be manufactured by cutting (e.g., laser cutting) the various features from a solid tube of superelastic Nitinol metal. In some aspects implant 10 may be finished by processes to remove slag.

Skilled artisans may implement the described functionality in varying ways for each particular application. Various components and blocks may be arranged differently (for example, arranged in a different order, or partitioned in a different way) all without departing from the scope of the subject technology. It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (for example, his) include the feminine and neuter gender (for example, her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "aspect" does not imply that such aspect is essential to the subject technology or that such aspect applies to all configurations of the subject technology. A disclosure relating to an aspect may apply to all aspects, or one or more aspects. An aspect may provide one or more examples. A phrase such as an "aspect" may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A medical device, comprising:
   a delivery wire having a proximal end and a distal end;
   a connection mechanism; and
   a vessel-engaging member attached to the distal end of the delivery wire via the connection mechanism, the vessel-engaging member comprising:
     a plurality of rows, each row having a plurality of struts arranged in an alternating pattern such that for each row, a first set of vertices is positioned on a proximal side, and a second set of vertices is positioned on a distal side;
     a plurality of bridges positioned between each adjacent row, each of the bridges connecting a vertex of a first row with a vertex of a second row, the vertex of the first row lying substantially along a line parallel to a longitudinal axis of the vessel-engaging member and the vertex of the second row lying outside the line, each of the bridges extending continuously distally from the vertex of the first row to the vertex of the second row, a cross-sectional width of each of the plurality of bridges being less than a cross-sectional width of each of the struts to which that bridge connects; and
   first and second tapered sections coupled to the connection mechanism, each of the tapered sections projecting from a proximal row and tapering in a direction from the proximal row toward the connection mechanism.

2. The medical device of claim 1, wherein each bridge has a bridge angle relative to the longitudinal axis of the member of between ten and fifty degrees.

3. The medical device of claim 1, wherein each of the plurality of struts has a strut length, each bridge has a bridge length, and the strut length is greater than the bridge length.

4. The medical device of claim 1, wherein each of the plurality of struts has a strut length, each bridge has a bridge length, and the strut length and the bridge length are the same.

5. The medical device of claim 1, wherein the device has a working region and at least one non-working region, the working region comprising the plurality of rows, the non-working region comprising a portion of the vessel-engaging member between the working region and the distal end of the delivery wire.

6. The medical device of claim 1, wherein the distal end of the delivery wire comprises a first connection wire and a second connection wire, wherein each of the first connection wire and the second connection wire is releasably connected to the vessel-engaging member.

7. A method of implanting a medical device in the neurovasculature comprising:
   inserting a guide catheter into the neurovasculature;
   inserting a microcatheter through the distal end of the guide catheter;
   inserting a vessel-engaging member into the microcatheter such that the distal portion of the member is located adjacent a treatment site in the neurovasculature, wherein the member comprises:
      a plurality of rows, each row having a plurality of struts arranged in an alternating pattern such that for each row, a first set of vertices is positioned on a proximal side and a second set of vertices is positioned on a distal side;
      a plurality of bridges positioned between each adjacent row, each of the bridges connecting a vertex of a first row with a vertex of a second row, the vertex of the first row lying substantially along a line parallel to a longitudinal axis of the vessel-engaging member and the vertex of the second row lying outside the line, each of the bridges extending continuously distally from the vertex of the first row to the vertex of the second row, a cross-sectional width of each of the plurality of bridges being less than a cross-sectional width of each of the struts to which that bridge connects;
      first and second tapered sections projecting from a proximal row and tapering in a direction from the proximal row toward a proximal end of the member; and
   withdrawing the microcatheter so as to expose and deploy the vessel-engaging member, the vessel-engaging member configured to expand against and engage the treatment site.

8. The method of claim 7, further comprising retrieving the vessel-engaging member by moving the microcatheter until the microcatheter covers a portion of the vessel-engaging member, and then withdrawing both the microcatheter and vessel-engaging member together proximally.

9. The method of claim 7, wherein expanding against and engaging the treatment site comprises extending the vessel-engaging member across a neck of an aneurysm, wherein the vessel-engaging member inhibits dislodging of objects out of the neck of the aneurysm.

10. The method of claim 9, further comprising inserting embolic material into a fundus of the aneurysm.

11. The method of claim 10, wherein inserting embolic material comprises inserting coils.

12. The method of claim 7, further comprising detaching the vessel-engaging member via a connection mechanism.

13. The method of claim 12, further comprising repositioning the vessel-engaging member prior to detachment.

14. The method of claim 7, wherein the treatment site comprises a lumen with tortuous curvature.

15. A method of implanting a medical device in a lumen at a tortuous curve, comprising:
   inserting a vessel-engaging member into the lumen, the member comprising:
      a plurality of rows, each row having a plurality of struts arranged in an alternating pattern such that for each row, a first set of vertices is positioned on a proximal side and a second set of vertices is positioned on a distal side;
      a plurality of bridges positioned between each adjacent row, each of the bridges connecting a vertex of a first row with a vertex of a second row, the vertex of the first row lying substantially along a line parallel to a longitudinal axis of the vessel-engaging member and the vertex of the second row lying outside the line, each of the bridges extending continuously distally from the vertex of the first row to the vertex of the second row, a cross-sectional width of each of the plurality of bridges being less than a cross-sectional width of each of the struts to which that bridge connects;
      first and second tapered sections projecting from a proximal row and tapering in a direction from the proximal row toward a proximal end of the member; and
   contacting a wall of the lumen with the member at an apex of the tortuous curve by deflecting the plurality of bridges adjacent to the apex so that vertices adjacent to the deflecting the plurality of bridges contact the wall of the lumen.

16. The method of claim 15, wherein contacting the wall of the lumen with the member at the apex comprises extending the vessel-engaging member across a neck of an aneurysm, and wherein the method further comprises inserting embolic material into a fundus of the aneurysm.

17. The method of claim 16, wherein inserting embolic material comprises inserting coils.

18. The method of claim 15, further comprising detaching the vessel-engaging member via a connection mechanism.

19. The method of claim 18, further comprising repositioning the vessel-engaging member prior to detachment.

\* \* \* \* \*